United States Patent [19]
Tilley et al.

[11] Patent Number: 5,922,325
[45] Date of Patent: Jul. 13, 1999

[54] SYNERGISTIC NEUTRALIZATION OF HIV-1 BY HUMAN MONOCLONAL ANTIBODIES AND OTHER ANTIBODIES DIRECTED AGAINST THE V3 LOOP AND THE CD-4 BINDING SITE OF GP-120, AND THE USE FOR IMMUNOTHERAPY OF HIV-1 INFECTION

[75] Inventors: Shermaine A. Tilley, New York; Abraham Pinter, Brooklyn, both of N.Y.

[73] Assignee: Public Health Research Institute of the City of New York, Inc., New York, N.Y.

[21] Appl. No.: 08/447,214

[22] Filed: May 22, 1995

Related U.S. Application Data

[63] Continuation of application No. 08/098,747, Jul. 28, 1993, abandoned, which is a continuation of application No. 07/715,336, Jun. 14, 1991, abandoned, which is a continuation-in-part of application No. 07/604,146, Oct. 26, 1990, abandoned.

[51] Int. Cl.$^6$ .......................... A61K 39/21; C12P 21/04; C12P 21/08
[52] U.S. Cl. ................... 424/208.1; 424/188.1; 424/142.1; 424/148.1; 424/160.1; 435/70.21; 435/346; 530/387.3
[58] Field of Search ............... 424/142.1, 148.1, 424/160.1, 183.1, 208.1, 188.1; 435/70.21, 172.2, 346; 530/387.3, 388.1, 388.35, 391.1, 391.7, 865

[56] References Cited

U.S. PATENT DOCUMENTS

| | | | |
|---|---|---|---|
| 4,725,669 | 2/1988 | Essex et al. | 530/322 |
| 4,772,547 | 9/1988 | Heimer et al. | 435/5 |
| 4,863,730 | 9/1989 | Karpas | 424/86 |
| 5,087,557 | 2/1992 | McClure | 435/5 |
| 5,166,050 | 11/1992 | Shriver et al. | 435/5 |

FOREIGN PATENT DOCUMENTS

| | | |
|---|---|---|
| 0199438 | 10/1986 | European Pat. Off. . |
| 0 279 688 | 2/1988 | European Pat. Off. . |
| 0 295 803 | 12/1988 | European Pat. Off. . |
| 0 311 219 | 4/1989 | European Pat. Off. . |
| 0339163 | 11/1989 | European Pat. Off. . |
| 0462551 | 12/1991 | European Pat. Off. . |
| 8809181 | 12/1988 | WIPO . |
| WO 90/15078 | 12/1990 | WIPO . |
| 9106575 | 5/1991 | WIPO . |
| 9109625 | 7/1991 | WIPO . |
| 9110742 | 7/1991 | WIPO . |
| 9113148 | 9/1991 | WIPO . |
| WO 91/15238 | 10/1991 | WIPO . |
| WO 91/17764 | 11/1991 | WIPO . |
| WO 91/18928 | 12/1991 | WIPO . |
| WO 93/04693 | 3/1993 | WIPO . |
| WO 93/08216 | 4/1993 | WIPO . |

OTHER PUBLICATIONS

Olshevsky, U., et al., "Identification of Individual Human Immunodeficiency Virus Type 1 gp120 Amino Acids Important for CD4 Receptor Binding," 64 (12) J. Virol. 5701–07 (1990).

Javaherian, et al., "Broadly Neutralizing Antibodies Elicited By the Hypervariable Neutralizing Determinant of HIV–1," 250 Sci. 1590–93 (1990).

(List continued on next page.)

*Primary Examiner*—Ponnathapura Achutamurthy
*Assistant Examiner*—Hankyel T. Park
*Attorney, Agent, or Firm*—Fish & Richardson P.C.

[57] ABSTRACT

A synergistic combination of antibodies specific for HIV envelope glycoprotein gp120 is described. One of the antibodies specific for the V3 loop and the other is specific for the CD-4 binding site of gp120.

53 Claims, 11 Drawing Sheets

OTHER PUBLICATIONS

LaRosa, G.J., et al., "Conserved Sequence and Structural Elements in the HIV–1 Principal Neutralizing Determinant," 249 Sci. 932–35 (1990).

Scott, C.F., et al., "Human Monoclonal Antibody That Recognizes the V3 Region of Human Immunodeficiency Virus gp120 and Neutralizes the Human T–Lymphotropic Virus Type III $_{MN}$ Strain," 87 Proc. Natl. Acad. Sci. USA 8597–8601 (1990).

Zolla–Pazner, S., et al., "Production of Human Monoclonal Antibodies Against the V3 Loop of gp120," Sixth Intl. Conf. on AIDS (Abstract, Th.A. 75) (San Francisco, CA 1990).

Sun, N., et al., "Generation and Characterization of Monoclonal Antibodies to the Putative CD4–Binding Domain of Human Immunodeficiency Virus Type 1 gp120," 63 (9) J. Virol. 3579–3585 (1989).

Lasky, L.A., et al., "Delineation of a Region of the Human Immunodeficiency Virus Type 1 gp120 Glycoprotein Critical for Interaction With the CD4 Receptor," 50 Cell 975–85 (1987).

Robinson, et al., "Antibodies to the Primary Immunodominant Domain of Human Immunodeficiency Virus Type 1 (HIV–1) Glycoprotein gp41 Enhance HIV–1 Infection In Vitro," 64(11) J. Virol. 5301–05 (1990).

Ho, et al., "Conformational Epitope on gp120 Important in CD4 Binding and Human Immunodeficiency Virus Type 1 Neutralization Identified by a Human Monoclonal Antibody," 65(1) J. Virol. 489–93 (1991).

Posner, M., et al., "Development of an IgG–1 Human Monoclonal Antibody That Neutralizes HIV1 Infectivity and Binding and Reacts With a Cell Surface Antigen Expressed by HIV1 Infected Cells," Sixth Intl. Conf. on AIDS, 153 (Abstract, Th.A.77 (San Francisco, CA 1990).

Robert–Guroff, M., et al., "HTLV–III–Neutralizing Antibodies in Patients with AIDS and AIDS–Related Complex," 316 Nature 72–74 (1985).

Weiss, R.A., et al., "Neutralization of Human T–Lymphotropic Virus Type III By Sera of AIDS and AIDS–Risk Patients," 316 Nature 69–71 (1985).

Rook, A.H., et al., "Sera From HTLV–III/LAV Antibody––Positive Individuals Mediate Antibody–Dependent Cellular Cytotoxicity Against HTLV–III/LAV–Infected T Cells," 138 J. Immunol. 1064–1067 (1987).

Ljunggren, K., et al., "Antibody–Dependent Cellular Cytotoxicity–Inducing Antibodies Against Human Immunodeficiency Virus," 139 J. Immunol. 2263–67 (1987).

Ho, D.D., et al., "Human Immunodeficiency Virus Neutralizing Antibodies Recognize Several Conserved Domains on the Envelope Glycoproteins," 61(6) J. Virol. 2024–38 (1987).

Devash, et al., "Vertical Transmission of Human Immunodeficiency Virus is Correlated With the Absence of High Affinity/Avidity Maternal Antibodies to the gp120 Principal Neutralizing Domain," 87 Proc. Natl. Acad. Sci. USA 3445–49 (1990).

Homsy, J., et al., "Antibody–Dependent Enhancement of HIV Infection," The Lancet 1285–86 (Jun., 1988).

Takeda, A., et al., "Antibody–Enhanced Infection By HIV–1 Via Fc Receptor–Meditated Entry," 242 Sci. 580–83 (1988).

Jouault, et al., "HIV Infection of Monocytic Cells: Role of Antibody–Mediated Virus Binding to Fc–Gamma Receptors," 3(3)AIDS 125–133 (1989).

Karpas, A., et al., "Effects of Passive Immunization In Patients With the Acquired Immunodeficiency Syndrome–Related Complex and Acquired Immunodeficiency Syndrome," 85 Proc. Natl. Acad. Sci. USA 9234–37 (1988).

Emini, et al., "Antibody–Mediated In Vitro Neutralization of Human Immunodeficiency Virus Type 1 Abolishes Infectivity for Chimpanzees'" 64(8) J. Virol. 3674–78 (1990).

Girard, et al., "Immunization of Chimpanzees Confers Protection Against Challenge With Human Immunodeficiency Virus," 88 Proc. Natl. Acad. Sci, USA 542–46 (1991).

Berman, et al., "Protection of Chimpanzees from Infection by HIV–1 After Vaccination with Recombinant Glycoprotein gp120 But Not gp160," 345 Nature 622–25 (1990).

Gerna, et al., "Synergistic Neutralization of Rubella Virus by Monoclonal Antibodies to Viral Haemagglutinin," 68 J. Gen. Virol. 2007–2012 (1987).

Volk, W.A., et al., "Monoclonal Antibodies to the Glycoprotein of Vesicular Stomatitis Virus: Comparative Neutralizing Activity," 42 (1) J. Virol. 220–27 (1982).

Peiris, J. S. M., et al., "Monoclonal Antibodies Against the Flavivirus West Nile," 58 J. Gen Virol. 283–89 (1982).

Cle gg, et al., "Conformational Changes In Sindbis Virus E1 Glycoprotein Induced By Monoclonal Antibody Binding," 64 J. Gen. Virol. 1121–1126 (1983).

Kimura–Kuroda, J., et al., "Topographical Analysis of Antigenic Determinants on Envelope Glycoprotein V3 (E) of Japanese Encephalitis Virus, Using Monoclonal Antibodies," 43(1) J. Virol. 124–32 (1983).

Kingsford, "Enhanced Neutralization of La Crosse Virus By the Binding of Specific Pairs of Monoclonal Antibodies to the G1 Glycoprotein," 136 Virol. 265–73 (1984).

Russell, P.H., "The Synergistic Neutralization of Newcastle Disease Virus By Two Monoclonal Antibodies To Its Haemagglutinin–Neuraminidase Protein," 90 Arch. Virol. 135–44 (1986).

Anderson, et al., "Neutralization of Respiratory Syncytial Virus by Individual and Mixtures of F and G Protein Monoclonal Antibodies," 62(11) J. Virol. 4232–38 (1988).

Dubuisson, et al., "Neutralization of Bovine Herpevirus Type 4 By Pairs of Monoclonal Antibodies Raised Against Two Glycoproteins and Identification of Antigenic Determinants Involved in Neutralization," 71 J. Gen. Virol. 647–653 (1990).

Chou, "The Median–Effect Principle and the Combination Index for Quantitation of Synergism and Antagonism," *Synergism and Antagonism in Chemotherapy*, 61–102 (San Diego, CA 1991).

Lussenhop, N.O., et al., "Epitope Analysis of Human Cytomegalovirus Glycoprotein Complexes Using Murine Monoclonal Antibodies," 164 Virol. 362–372 (1988).

Layne, S.P., et al., "Quantifying the Infectivity of Human Immunodeficiency Virus," 86 Proc. Natl. Acad. Sci. USA 4644–48 (1989).

Gorny, M.K., et al., "Generation of Human Monoclonal Antibodies To Human Immunodeficiency Virus," 86 Proc. Natl. Acad. Sci. USA 1624–28 (1989).

Tilley, S.A., et al., "A Human Monoclonal Antibody Against the CD4 Binding Site of HIV–1 gp120 Exhibits Potent, Broadly Neutralizing Activity," 142 Res. Virol. 247–259 (Paris 1991).

Kieny, M.P., et al., "Improved Antigenicity of the HIV env Protein By Cleavage Site Removal," 2(3) Protein Eng. 219–225 (1988).

Leonard, C.K., et al., "Assignment of Intrachain Disulfide Bonds and Characterization of Potential Glycosylation Sites of the Type 1 Recombinant Human Immunodeficiency Virus Envelope Glycoprotein (gp120) Expressed in Chinese Hamster Ovary Cells," 265 J. Biol. Chem. 10373–10382 (1990).

Gurgo, C., et al., "Envelope Sequences of Two New United States HIV–1 Isolates," 4164 Virology 531–36 (1988).

Harada, S., et al., "Infection of HTLV–III/LAV in HTLV–I–Carrying Cells MT–2 and MT–4 and Application in a Plaque Assay," 229 Sci. 563–66 (1985).

Robinson, J.E., et al., "Identification of Conserved and Variant Epitopes of Human Immunodeficiency Virus Type 1 (HIV–1) gp120 by Human Monoclonal Antibodies Produced by EBV–Transformed Cell Lines," 6 (5) AIDS Res. Human Retroviruses 567–79 (1990).

Ho, D.D., et al., "A Neutralizing Human Monoclonal Antibody (HMab) Identifies an Epitope Within the Putative CD4–Binding Domain (CD4–BD) of HIV–1 gp120," Sixth Intl. Conf. on AIDS. 152 (CA 1990).

Gallo, R., et al., "Frequent Detection and Isolation of Cytopathic Retroviruses (HTLV–III) from Patients with AIDS and At Risk for AIDS," 224 Sci. 500–503 (1984).

Berzofsky, J.A., et al. "Antigen–Antibody Interactions and Monoclonal Antibodies," Fundamental Immunology, 315–356 (NY 1989).

Mosier, et al., "Transfer of a Functional Human Immune System to Mice With Severe Combined Immunodeficiency," 335 Nature 256–259 (1988).

McCune, et al., "The SCID–hu Mouse: Murine Model for the Analysis of Hum Hematolymphoid Differentiation and Function." 241 Sci. 1632–1639 (1988).

Teng, N. N. H., et al., "Construction and Testing of Mouse––Human Heteromyelomas for Human Monoclonal Antibody Production," 80 Proc. Natl. Acad Sci. USA 7306–12 (1982).

Kozbur, D., et al. "Human Hybridomas Constructed With Antigen–Specific Epstein–Barr Virus–Transformed Cell Lines," 79 Proc. Natl. Acad. Sci. USA 6651–55 (Nov. 1982).

Larrick, J.W., et al. "Polymerase Chain Reaction Using Mixed Primers: Cloning of Human Monoclonal Antibody Variable Region Genes From Single Hybridoma Cells," 7 Biotech. 934–38 (Sep. 1989).

Orlandi, R., et al. "Cloning Immunoglobulin Variable Domains for Expression By the Polymerase Chain Reaction," 86 Proc. Natl. Acad. Sci. USA 3833–37 (May 1989).

Shuford, et al., "Effect of Light Chain V Region Duplication on IgG Oligomerization and In Vivo Efficacy," 252 Sci. 724–727 (1991).

Raubitschek, A.A., "Epstein–Barr Virus Transformation," *Human Hybridomas and Monoclonal Antibodies*, 454–55 (New York, 1985).

Coller, H.A., et al., "Statistical Assessment of Hybridoma Monoclonalit After Subcloning By the Limiting Dilution Technique," *Methods of Hybridoma Formation*, 231–36 (N.J. 1987).

Eckhardt, L.A., et al., "DNA Rearrangements in MPC–11 Immunoglobulin Heavy Chain Class–Switch Variants," 79 Proc. Natl. Acad. Sci. USA 3006–3010 (May 1982).

Ravetch, J.V., et al., "Structure of the Human Immunoglobulin $\mu$ Locus: Characterization of Embryonic and Rearranged J and D Genes," 27 Cell 583–591 (Dec. 1981).

Pinter, A., et al. "Oligomeric Structure of gp41, The Transmembrane Protein of Human Immunodeficiency Virus Type 1," 63(6) J. Virol. 2674–79.

Pinter, A., et al. "O–Linked Glycosylation of Retroviral Envelope Gene Products," 62(3) J. Virol 1016–21 (Mar. 1988).

Laemmli, U.K., "Cleavage of Structural Proteins During the Assembly of the Head of Bacteriophage T4," 227 Nature 680–83 (Aug. 1970).

Bonner, W.M., et al. "A Film Detection Method for Tritium––Labelled Proteins and Nucleic Acids in Polyacrylamide Gels," 46 Eur. J. Biochem. 83–88 (1974).

Popovic, M., et al., "Detection, Isolation, and Continuous Production of Cytopathic Retroviruses (HTLV–1–Carrying Cells MT–2 and MT–4 and Application in a Plaque Assay," 224 Sci. 497–500, equivalent to Report, 151–58 (May 1984).

Ratner, L., et al., "Complete Nucleotide Sequence of the AIDS Virus, HTLV–III," 313(24) Nature 277–284 (1985).

Levy, J.A., et al., "Isolation of Lymphocytopathic Retroviruses from San Francisco Patients with AIDS," 225 Sci. 840–42 (Aug. 1984).

Sanchez–Pescador, R., et al., Nucleotide Sequence and Expression of an AIDS–Associated Retrovirus, 227 Sci. 484–492 (Feb. 1985).

Shaw, G.M., et al., Molecular Characterization of Human T–Cell Leukemia (Lymphotropic) Virus Type III in the Acquired Immune Deficiency Syndrome 226 Sci. 1165–71 (Dec. 1984).

Starcich, B.R., et al. "Identification and Characterization of Conserve and Variable Regions in the Envelope Gene of HTLV–111/LAV, the Retrovirus of AIDS," 45 Cell 637–48 (Jun. 1986).

Clavel, F., et al., "Isolation of a New Human Retrovirus from West African Patients With AIDS," 233 Sci. 343–46 (Jul. 1986).

Siadak, A.W., et al., "Cell–Driven Viral Transformation," *Human Hybridomas and Monoclonal Antibodies*, 167–185 (NY 1985).

Dolby, T.W., et al., "Cloning and Partial Nucleotide Sequence of Human Immunoglobulin $\mu$Chain cDNA from B Cell and Mouse–Human Hybridoma.," 77(10) Proc. Natl. Acad. Sci. USA 6027–31 (Oct. 1980).

Van Heyningen, V., et al., "Ranking the Affinities of Monoclonal Antibodies," *Methods of Hybridoma Formation*, 399–411 (Clifton, 1987).

Koyanagi, et al., "Dual Infection of the Central Nervous System by AIDS Viruses and Distinct Cellular Tropisms," 236 Sci. 819–22 (1987).

Chou, T. and Talalay, P.,"Quantitative Analysis of Dose–Effect Relationships: The Combined Effects of Multiple Drugs or Enzyme Inhibitors," 22 Adv. in Enz. Reg. 27–55 (1984).

Groopman, et al., "Characterization of Serum Neutralization Response to the Human Immunodeficiency Virus (HIV)," 3(1) AIDS Res. and Human Retro. 71–85 (1987).

Berman, P.W., et al., "Expression and Immunogenicity of the Extracellular Domain of the Human Immunodeficiency Virus Type 1 Envelope Glycoprotein, gp160," 63(8) J. Virol. 3489–3498 (1989).

Crawford, D.H., "Production of Human Monoclonal Antibodies Using Epstein–Barr Virus," *Human Hybridomas and Monoclonal Antibodies*, 37–53 (NY 1985).

Tilley et al., "Broadly Neutralizing Human Monoclonal Antibody Against HIV gp120," accepted in Retroviruses of Human AIDS and Related Animal Diseases, Cinquieme Colloque Des 'Cent Gardes', Marnes–la–Coquette, (France 1990).

Tilley, et al., "Human Monoclonal Antibodies Against the Putative CD4 Binding Site and the V3 Loop of HIV gp120 Act in Concert to Neutralize Virus." Abstract Form to VII Int'l. Conf. on AIDS (Italy, Jun. 16–21, 1991).

Kawamura, T., "A Hybridoma Producing Human Monoclonal IgG Neutralizes the HTLVIIb Isolate In Vitro," V Intl Conf. on AIDS, Abstract #TH.C.O.4. (Montreal Jun., 1989).

Skinner, et al., "Neutralizing Antibodies to an Immunodominant Envelope Sequence Do Not Prevent gp120 Binding to CD4," 62(11) Jl. Virol 4195–4200 (Nov. 1988).

Nara, et al., "Emergence of Viruses Resistant to Neutralization by V3–Specific Antibodies in Experimental Human Immunodeficiency Virus Type 1 IIIB Infection of Chimpanzees," 64(8) Jl. Virol 3779–3791 (Aug. 1990).

Sugita, et al., "Use of a Cocktail of Monoclonal Antibodies and Human Complement in Selective Killing of Acute Lymphocytic Leukemia Cells," 37 Intl Jl. Cancer 351–57 (1986).

Folks, "Epitope Mapping of Human Immunodeficiency Virus: A Monoclonal Approach," 139(12) Jl. of Immunol. 3913–3914 (Dec. 1987).

Olsnes, "Chimeric Toxins," 15 Pharmac. Ther. 355–381 (1982).

PCT International Search Report, Int'l Publication No. WO 92/07878; International Application No. PCT/US91/07910.

Tilley, et al. "Synergistic neutralization of HIV–1 by human monoclonal antibodies against the V3 loop and the CD 4 binding site of gp120" 8 AIDS Res. and Human Retro. 461–467 (1992).

Gorny, et al., "Production of site–selected neutralizing human monoclonal antibodies against the third variable domain of the human immunodeficiency virus type 1 envelope glycoprotein", 88 Proc. Natl. Acad. Sci. USA 3238–3242 (Apr. 1991).

Matsushita, S.M., et al., "Characterization of a human immunodeficiency virus neutralizing monoclonal antibody and mapping of the neutralization epitope" 61 J. Virol. 2107–2114 (1988).

D'Souza, M.P., et al., "Evaluation of monoclonal antibodies to HIV–1 by neutralization and serological assays: an international collaboration" 5 AIDS 1061–1070 (1991).

Zolla–Pazner et al., "Type–specific and group specific antibodies to HIV: The decline and fall of an oversimplified concept", Abstract from Keystone Conf., (1992).

Andris et al., "Molecular characterization of five human anti–human immunodeficiency virus type 1 antibody heavy chains reveals extensive somatic mutation typical of an antigen–drive response", 88 Proc. Natl. Acad. Sci. USA 7783–77878 (Sep. 1991).

Buchbinder et al., "Synergy between human monoclonal antibodies to HIV extends their effective biological activity against homologous and divergent strains", AIDS Res. and Human Retro. 461–467 (1992).

Buchacher et al., "Human monoclonal antibodies against gp41 and gp120 as potential agent for passive immunization", Vaccines 92, Cold Spring Harbor Laboratory Press, Cold Spring Harbor (1992).

Burton et al., "A large array of human monoclonal antibodies to type 1 human immunodeficiency virus from conbinatorial libraries of asymptomatic seropositive individuals," 88 proc. Natl. Acad. Sci. 10134–10137 (1991).

Emini et al., "Prevention of HIV–1 infection in chimpanzees by gp 120 V3 domain specific monoclonal antibody", 355 Nature 728–730 (1992).

Girard et al., "Immunization of chimpanzees against HIV–1 provides protection against cell–free and cell–associated virus challenge", Sixieme Colloque Des Cent Gards (1991).

Gorny et al., "Human monoclonal antibodies (HumAbs) to the V3 loop of HIV–1 react with divergent strains", abstract, Florence Int'l. Conf. on HIV (Jun. 19, 1991).

Jackson et al., "Passive Immunoneutralisation of human immunodeficiency virus in patients with advanced AIDS", Lancet 647–651 (Sep. 17, 1988).

Kang et al., "Evidence for non–V3 specific neutralizing antibodies that interfere with gp120/CD4 binding in human immunodeficiency virus 1 infected humans", 88 Proc. Natl. Acad. Sci. 6171–6175 (Jul. 1991).

Karpas et al., "Polmerase chain reaction evidence for human immunodeficiency virus 1 neutralization by passive immunization in patients with AIDS and AIDS–related complex", 87 Proc. Natl. Acad. Sci. 7613–7617 (Oct. 1990).

Karkowska et al., "Passive Immunization for the treatment and prevention of IV infection", 2(1–1) Biotechnology Therepeutics 31–48 (1991).

Koup et al., "Antibody–dependent cell–mediated cytotoxicity directed by a human monoclonalantibody reactive with gp120 of HIV–1", 5(11) AIDS 1309–1314 (1991).

Lake et al., "Generation and characterization of a human monoclonal antibody that neutralizes diverse HIV–1 isolates in vitro", 6(1) AIDS 17–24 (1992).

Pinter, et al., "Mechanism of synergistic neutralization of HIV–1 by human monoclonalantibodies (HumAbs) against the V3 loop and CD4 binding site of gp120", Abstract Netherlands Int'l Conf. on AIDS (1992).

Posner et al., "An IgG human monoclonal antibody that reacts with HIV–1/gp120, inhibits virus binding to cells, and neutralizes infection", 146 J. Imm. 4325–5332 (Jun. 15, 1991).

Posner et al., "Functional activity of an HIV–1 Neutralizing IgG human monoclonal antibody: ADCC and Complement-–Mediated Lysis", 8(5) AIDS Res. and Human Retro. 553–558 (1992).

Posner et al., "Human Monoclonal antibodies to the V3 loop of gp120 mediate variable and distinct effects on binding and viral neutralization by a human monoclonal antibody to the CD4 binding site", Abstract, Keystone Conf. on Prevention and Treatment of AIDS (1992).

Potts et al., "Synergistic inhibition of HIV–1", Abstract, Keystone Conf. on Prevention and Treatment of AIDS (1992).

Prince et al., "Prevention of HIV infection by passive immunization with HIV immunoglobulin", 7(12) AIDS Res. and Human Retro. 971–973 (1992).

Robinson et al., "Distinct antigenic sites on HIV gp 120 identified by a panel of human monoclonal antibodies", Abstract, Keystone Conf. of Prevention and Treatment of AIDS (1992).

Rossi et al., "Presence of maternal antibodies to human immuno–deficiency virus 1 envelope glycoprotein gp 120 epitopes correlates with the uninfected status of children born to seropositive mothers", 86 Proc. Natl. Acad. Sci. 8055–8058 (Oct. 1989).

Takeda et al., "Distinction of HIV–1 neutralization and invention enhancement by human monoclonal antibodies to gp120", in press J. Clin. Inv. (1992).

Thali et al., "Characterization of a discontinuous human immunodeficiency virus type 1 gp120 epitope recognized by a broadly reactive neutralizing human monoclonal antibody", J. Vir. 6188–6193 (Nov. 1991).

Thali et al., "Cooperativity of neutralizing antibodies directed against the V3 and CD4 binding regions of the human immunodeficiency virus gp120 envelope glycoprotein", 5 J. Acq. Imm. Def. Synd. 591–599 (1992).

Thali et al., "Discontinuous, conserved neutralization epitopes overlapping the CD4 binding region of human immunodeficiency virus type 1 of gp120 envelope glyco- –protein", J. Vir. 5635–5641 (1992).

Tilley et al., "Potent neutralization of HIV–1 by human and chimpanzee monoclonal antibodies directed against three distinct epitope clusters of gp120", Sixieme Colloque Des Cent Gardes (1991).

Tilley et al., "Synergistic neutralization of HIV–1 by combinations of antibodies specific for different epitope clusters of gp120", Abstract, Keystone Conf. on Prevention and Treatment of AIDS (1992).

Tilley et al., "Very broadly neutralizing human monoclonal antibody (HumAb) against the CD binding site of HIV–1 gp120", Abstract, Netherlands Int'l Conf. of AIDS (1992).

Ward et al., "Prevention of HIV–1 IIIB Infection in chimpanzees by CD4 immunadhesin", 352 Nature 434–438 (Aug. 1991).

Karwowska, et al., "Type–specific" Human Monoclonal Antibodies Cross–react with the V3 Loop of Various HIV–1 Isolates, Vaccines 92, Cold Spring Harbor Laboratory Press, 171–174 (1992).

Posner et al, "An IgG Human Monoclonal Antibody that Reacts with HIV–1/GP 120, Inhibits Virus Binding to Cells, and Neutralizes Infection," Jun. 15, 1991, Journal of Immunology, vol. 146. 4325–4322.

Thali et al, "Characterization of a Discontinuous Human Immunodeficiency Virus Type 1 gp120 Epitope Recognized by a Broadly Reactive Neutralizing Human Monoclonal Antibody," Nov. 1991, Journal of Virology, vol. 65,1, 6188–6193.

Posner et al, "Functional Activity of an HIV–1 Neutralizing IgG Human Monoclonal Antibody: ADCC and Complement–Mediated Lysis,", Mar. 28, 1992, Aids Research and Human Retroviruses, vol. 8, 5.

Thali et al, "Discontinuous, Conserved Neutralization Epitopes Overlapping the CD4–Binding Region of Human Immunodeficiency Virus Type 1 gp120 Envelope Glycoprotein," Sep. 1992, Journal of Virology, vol. 66,9, 5635–5641.

Lake et al., "Generation and characterization of a human monoclonal antibody that neutralizes diverse HIV–1 isolates in vitro," 1992, AIDS 6:17–24.

Tilley et al, "Human and Chimpanzee Monoclonal Antibodies with Antiviral Activity Against HIV–1," 1993, AIDS Research Reviews, Marcel Decker, NY, pp. 255–287.

Potts et al, "Potency and Broadness of Neutralization of HIV–1 By α–V3 Mabs is Enhanced by Synergy withCD4 and Cell Killing With α–CD3 Mabs," Jul. 19–24, 1992, VIII Int'l Conference on AIDS.

Emini et al., "Prevention of HIV–1 infection in chimpanzees by gp120 V3 domain–specific monoclonal antibody," Feb. 1992, Nature, 355:728–730.

Safrit et al., "hu–PBL–SCID mice can be protected from HIV–1 infection by passive transfer of monoclonal antibody to the principal neutralizing determinant of envelope gp120," 1993, AIDS, 7:15–21.

Robinson et al., "Identification of Conserved and Variant Epitopes of Human Immunodeficiency Virus Type 1 (HIV–1) gp120 by Human Monoclonal Antibodies Produced by EBV–Transformed Cell lines," *AIDS Res. Human Retroviruses* 6(5):562–579, 1990.

Sugita et al., "Use of a Cocktail of Monoclonal Antibodies and Human Complement in Selective Killing of Acute Lymphocytic Leukemia Cells" *Int. J. Cancer* 37: 351–357, 1986.

Tilley et al., "Human Monoclonal Antibodies Against the Putative CD4 Binding Site and the V3 Loop of HIV gp120 Act in Concert to Neutralize Virus," *VII International Conference on AIDS*, Florence, Italy, Abstract No. M.A.70, Jun. 16, 1991.

APPARENT AFFINITY CONSTANTS OF HUMAN anti-gp 120 mAbs

| mAb | 1/K | K |
|---|---|---|
| 1125H | $7.8 \times 10^{-10}$ M | $1.3 \times 10^9$ L/mole |
| 2173C | $5.3 \times 10^{-10}$ M | $1.9 \times 10^9$ L/mole |
| 2154B.1 | $1.5 \times 10^{-9}$ M | $6.8 \times 10^8$ L/mole |
| 4117C | $1.1 \times 10^{-9}$ M | $9.0 \times 10^8$ L/mole |

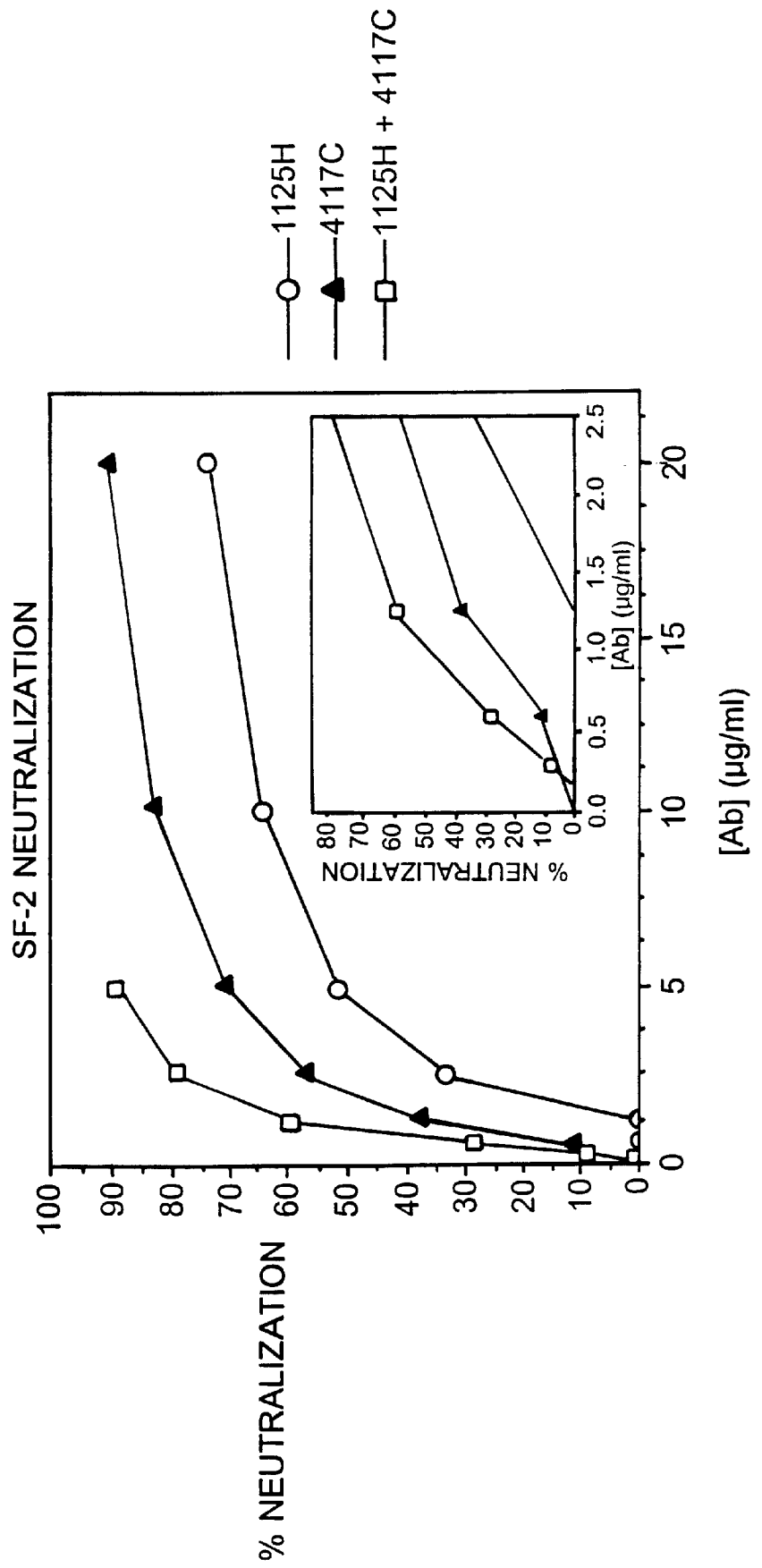

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 6 amino acids

```
            (B) TYPE: amino acid
            (C) STRANDEDNESS: Not Relevant
            (D) TOPOLOGY: linear (xi) SEQUENCE DESCRIPTION: SEQ ID NO:1:

Gly Pro Gly Arg Ala Phe
    1               5

(2) INFORMATION FOR SEQ ID NO:2:

(i) SEQUENCE CHARACTERISTICS:
            (A) LENGTH: 25 amino acids
            (B) TYPE: amino acid
            (C) STRANDEDNESS: Not Relevant
            (D) TOPOLOGY: linear (xi) SEQUENCE DESCRIPTION: SEQ ID NO:2:

Asn Tyr Asn Lys Arg Lys Arg Ile His Ile Gly Pro Gly Arg Ala
    1               5                   10                  15

Phe Tyr Thr Thr Lys Asn Ile Ile Gly Cys
                    20                  25

(2) INFORMATION FOR SEQ ID NO:3:

(i) SEQUENCE CHARACTERISTICS:
            (A) LENGTH: 4 amino acids
            (B) TYPE: amino acid
            (C) STRANDEDNESS: Not Relevant
            (D) TOPOLOGY: linear (xi) SEQUENCE DESCRIPTION: SEQ ID NO:3:

Gly Pro Gly Arg
    1

(2) INFORMATION FOR SEQ ID NO:4:

(i) SEQUENCE CHARACTERISTICS:
            (A) LENGTH: 3 amino acids
            (B) TYPE: amino acid
            (C) STRANDEDNESS: Not Relevant
            (D) TOPOLOGY: linear (ix) FEATURE:
            (D) OTHER INFORMATION: Xaa is any amino acid.

(xi) SEQUENCE DESCRIPTION: SEQ ID NO:4:

Ile Xaa Ile
    1

(2) INFORMATION FOR SEQ ID NO:5:

(i) SEQUENCE CHARACTERISTICS:
            (A) LENGTH: 7 amino acids
            (B) TYPE: amino acid
            (C) STRANDEDNESS: Not Relevant
            (D) TOPOLOGY: linear (ix) FEATURE:
            (D) OTHER INFORMATION: Xaa is any amino acid.

(xi) SEQUENCE DESCRIPTION: SEQ ID NO:5:

Ile Xaa Ile Gly Pro Gly Arg
    1               5
```

SYNERGISTIC NEUTRALIZATION OF HIV-1 BY HUMAN MONOCLONAL ANTIBODIES AND OTHER ANTIBODIES DIRECTED AGAINST THE V3 LOOP AND THE CD-4 BINDING SITE OF GP-120, AND THE USE FOR IMMUNOTHERAPY OF HIV-1 INFECTION

This is a continuation of application Ser. No. 08/098,747 filed on Jul. 28, 1993, now abandoned, which is a continuation of Ser. No. 07/715,336, filed Jun. 14, 1991, now abandoned, which is a continuation-in-part of Ser. No. 07/604,146, filed Oct. 26, 1990, now abandoned.

FIELD OF THE INVENTION

This invention relates to antibodies ("Abs") having neutralizing capabilities against HIV-1.

BACKGROUND OF THE INVENTION

A major problem for immunological approaches to the control of HIV is the extreme variability of the viral genome, which is reflected in a corresponding antigenic variability. This problem has hampered attempts to design effective vaccines as well as attempts to develop immunotherapies. It is, thus, well recognized that the identification of neutralizing but non-variable epitopes would constitute a major advance in this area.

The HIV envelope is composed of two glycoproteins, gp120 and gp41. These glycoproteins are initially synthesized in virus-infected cells as a precursor called gp160; this molecule is cleaved into gp120 and gp41 prior to assembly of virions. The latter two glycoproteins are non-covalently associated with each other and are anchored to the viral membrane via gp41, a transmembrane protein (reviewed in (Olshevsky et al. 1990)).

One region which has been shown to elicit neutralizing antibodies is the V3 region hypervariable loop (hvl-V3) of the gp120 (amino acids 307–330); this is an immunodominant epitope cluster eliciting potent neutralizing Abs in man and experimental animals (summarized in (Javaherian et al. 1990)). Initially, there was the concern that the hypervariability of the V3 loop would prevent the design of a rational vaccine based on this epitope. However, LaRosa et al. (LaRosa et al. 1990) have recently shown that the V3 loop is less variable than originally thought, and, in addition, anti-V3 Abs with broader HIV strain specificity have been generated (Javaherian et al. 1990); these Abs recognize a conserved hexamer sequence (Gly Pro Gly Arg Ala Phe (SEQ ID NO:1) present at the tip of the loop. Three anti-V3 human monoclonal antibodies (HuMAbs) have been isolated by other investigators, and each is relatively strain-specific, recognizing only the MN strain of virus and closely related strains (Scott et al. 1990, Zolla-Pazner et al. 1990).

Another epitope cluster of HIV envelope that has been shown to elicit neutralizing antibodies is the CD4 binding site of gp120. Recent evidence indicates that the CD4 binding site is formed by non-contiguous protein loops from multiple regions of gp120 (Olshevsky et al. 1990). However, the precise structure of the CD4 binding site and its contact residues have yet to be defined. Neutralizing antibodies against this site have been raised in some rodents (Sun et al. 1989, Lasky et al. 1987, Berman et al. 1989) using either recombinant gp120 or linear peptides adjacent to one of the loops apparently forming the CD4 binding site. It was believed that humans do not produce Abs against the CD4 binding site, partially because no human serum Abs could be shown to bind to the linear peptides discussed above (Sun et al. 1989, Lasky et al. 1987). We and two other groups (Robinson et al. 1990, Ho et al. 1991, Posner et al. 1990) have isolated HuMAbs against conformational, rather than linear, epitopes mapping in the CD4 binding region. These HuMAbs have neutralizing activity against a variety of divergent HIV-1 strains and, therefore, recognize relatively conserved epitopes.

Earlier in the AIDS epidemic, there was skepticism about the protective function of neutralizing Abs against HIV, since such Abs could be found in seropositive individuals who went on to develop AIDS. Now it is understood that the titers of neutralizing Abs developed in humans during the course of HIV infection are generally not very high (Robert-Guroff et al. 1985, Weiss et al. 1985), that higher titers of certain anti-HIV Abs do correlate with a better prognosis (Robert-Guroff et al. 1985, Rook et al. 1987, Ljunggren et al. 1987, Ho et al. 1987, Devash et al. 1990), and that deleterious Abs against HIV that actually enhance viral infection may be present in seropositive individuals (Robinson et al. 1990, Homsy et al. 1988, Takeda et al. 1988, Jouault et al. 1989). Furthermore, recent studies demonstrate the protective effects of certain anti-HIV Abs in vivo. In one such study, passive administration of hyperimmune plasma from healthy HIV-infected humans to ARC and AIDS patients resulted in sustained clearance of p24 antigen and a maintenance or increase in the recipients' anti-viral Ab titer, and clinical improvement was noted in 5 of 9 recipients (Karpas et al. 1988). In another study, chimpanzees were challenged with a stock of the IIIB strain of HIV that had previously been incubated with neutralizing serum Ab from an HIV-seropositive chimpanzee. The challenged animals were protected against viral infection, as assessed by lack of serum Ab response to virus and attempts at viral isolation (Emini et al. 1990). Very recently, successful long term protection of two chimpanzees against HIV infection has been demonstrated by immunization with recombinant gp160 followed by a V3 loop peptide (Girard et al. 1991). In a different study, chimpanzees immunized with recombinant gp120 and challenged with HIV were also protected from infection (Berman et al. 1990). In both of these vaccine trials, significant titers of strain-specific neutralizing Ab were induced prior to challenge with virus. The protection obtained is believed to be due primarily to this neutralizing Ab, since subunit vaccines are thought to be poor inducers of cytotoxic T cells (see (Berman et al. 1990)).

Viral neutralization by combinations of rodent mabs has been described for certain non-AIDS viruses, including rubella (Gerna et al. 1987), vesicular stomatitis (Volk et al. 1982), West Nile (Peiris et al. 1982), Sindbis (Clegg et al. 1983), Japanese encephalitis (Kimura-Kuroda and Yasui 1983), La Crosse (Kingsford 1984), Newcastle disease (Russell 1986), respiratory syncytial (Anderson et al. 1988), and bovine herpesvirus type 4 (Dubuisson et al. 1990) viruses. In these studies, relatively high levels of viral neutralization are attained by relatively low concentrations of two or more mAbs in combination than is attained by any of the mAbs alone.

To our knowledge, however, improved neutralization of HIV by a combination of Abs has not been reported, nor has anyone previously demonstrated synergistic neutralization of any virus by human mAbs.

SUMMARY OF THE INVENTION

The present invention relates to a synergistic combination of HIV-1 obtained by a combination of certain antibodies specific for HIV-envelope glycoprotein gp120 and the therapeutic use of that combination.

One of the Abs in the combination is specific for the V3 loop of HIV-1 envelope glycoprotein gp120. The other is specific for the CD-4 binding site of HIV-1 envelope glycoprotein gp120. The invention included all Abs which are specific for epitopes within these epitope clusters which, when combined, are capable of synergistically neutralizing HIV-1 infection. Preferably the antibodies are human monoclonal antibodies, but the invention relates to other types of antibodies as well.

The synergistic combination of human mAbs is preferably capable of achieving 95% neutralization of about $1\times10^4$ infectious units of the MN strain of HIV-1 at a concentration of about 0.5 micrograms/ml.

Preferred embodiments of the invention include the synergistic combinations of: human mabs which competitively inhibit, in vitro, the binding of antibodies produced by the cell line 1125H to gp120, and human mAbs which competitively inhibit, in vitro, the binding of antibodies produced by the cell line 4117C to gp120, and which are capable of synergistically neutralizing HIV infection. Preferably, the combination is capable of about 95% neutralization of about $1\times10^4$ infectious units of the MN strain of HIV-1 at a concentration of about 0.5 micrograms/ml.

The antibody combination can be used for treatment or prevention of HIV infection. Preferably, the antibodies are used together, but they may be administered sequentially.

Also included in the invention is a cell line which produces human monoclonal antibodies specific for the V3 loop of HIV-envelope glycoprotein gp120, which antibodies have the epitope specificity of those produced by the cell line 4117C to gp120.

BRIEF DESCRIPTION OF THE DRAWINGS

FIG. 7 depicts the synergistic neutralization of the SF-2 strain by human nabs 1125H and 4117C.

DETAILED DESCRIPTION OF THE INVENTION

The specification of our pending application, Ser. No. 07/604,146, filed Oct. 26, 1990, is hereby incorporated by reference.

We have discovered that when certain antibodies to the anti-CD4 binding site region and certain antibodies to the anti-V3 region are combined they act synergistically, that is they neutralize HIV at much lower concentrations than those needed for the individual antibodies.

Theoretical considerations indicate that the quantities of single Abs required to inhibit virus spread in vivo in infected individuals may be high and not readily obtainable. The enhanced activity of the combination that we have discovered overcomes this problem.

To our knowledge, we are the first to observe synergistic neutralization of HIV by a combination of Abs and the first to demonstrate synergistic neutralization of any virus by human mabs. Further, we have obtained these results for two of the most prevalent HIV strains in the United States, MN and SF-2.

We have mathematically analyzed the degree of synergism obtained in these experiments with two of our neutralizing human mAbs: 4117C, an anti-V3 human mAb, and 1125H, an anti-CD4 binding site human mAb. Results of these analyses indicate that the synergism which we have observed between 1125H and 4117C against HIV. is as great as any yet seen between any two drugs or reagents, i.e., combination index (CI) values of 0.01–0.2 (Chou 1991).

These two human MAbs, when combined in a 1:1 ratio, neutralize 95–99% of the HIV. virions at a dose reduction index ranging from 30–150. This means that the same level of neutralization is attained by 30–150 fold less total human mAb when used in combination rather than when either is used alone.

The fact that these particular mAbs of the invention are of human origin means that they have distinct advantages for use as an anti-viral drug in humans. These reagents possess a number of advantages over rodent MAbs for this purpose, including increased stability and very low immunogenicity in humans. Thus, human MAbs are much less likely to create deleterious anti-immunoglobulin responses than are mAbs from other species such as rodents, and it should be possible to obtain stable levels of therapeutic doses of human mAbs in humans.

Because of the significance of these observations, we have attempted to determine the theoretical mechanism underlying our discovery. Such knowledge might reduce the effort for one skilled in the art to optimize our invention.

Figures 4, 5:
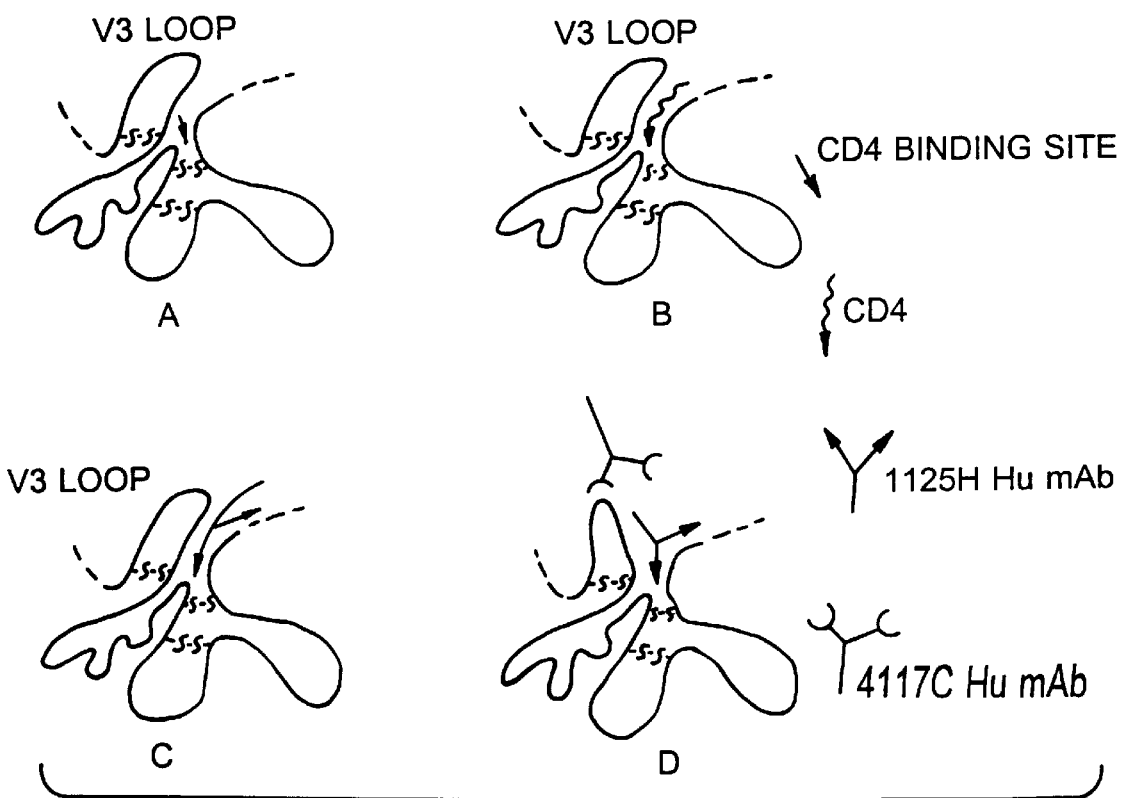
FIG. 4 depicts the apparent affinity of human mAbs 1125H, 2173C, 2154B.1, and 4117C.
FIG. 5 depicts a hypothetical binding scenario for the 1125H and 4117C antibodies.

One mechanism by which the synergism could occur is by enhanced binding of one or both of the Abs to gp120 in the presence of the other Ab. Using a binding assay wherein recombinant gp160 (containing the relevant gp120 epitopes) is immobilized on ELISA plates, we have demonstrated a two-three fold enhancement of binding of the 1125H human mAb to its epitope in the presence of 4117C. In contrast, the binding of 4117C to its epitope is not affected by the presence of 1125H over the same concentration range. Such a unidirectional enhancement of binding has been observed for pairs of mabs participating in synergistic neutralization of La Crosse (Kingsford 1984) and rubella (Gerna et al. 1987) viruses. Assuming that the enhanced binding of 1125H induced by 4117C occurs on multiple gp120 molecules on a single virion, it could easily account for the potent synergism observed between 4117C and 1125H in HIV neutralization (Lussenhop 1988). At this time, our hypothesis for the theory underlying the invention is that the CD4 binding site becomes more accessible to the 1125H Ab when the 4117C Ab is bound to the V3 loop, whereas the V3 loop is equally accessible to 4117C whether 1125H is bound to the CD4 binding site or not (FIG. 5). This model fits with current conceptions of the V3 loop as an accessible, immunodominant epitope cluster and the CD4 binding site as a less immunogenic, possibly buried, epitope cluster. Furthermore, the model may explain observations on the human humoral immune response to these neutralizing epitopes. Specifically, it has been observed that individuals infected with HIV produce Abs against the V3 loop within a few weeks following infection, whereas antibodies against the CD4 binding site typically do not appear for months following infection. Our model suggests that the CD4 binding site may become more immunogenic following the production of anti-V3 Abs in vivo, since the latter's binding to V3 may make the CD4 binding site more accessible to the immune system.

The invention includes the use of polyclonal antibodies against the CD4 binding site and V3 regions, as well as the use of human mAbs against these regions. We have demonstrated that chimp polyclonal antibodies against the V3 region also synergize in this manner.

An important advantage of the use of human mAbs instead of total serum antibodies for immunotherapy, however, is that the monoclonal antibody technology allows us to produce unlimited amounts of homogeneous reagents. The reagents may be further characterized and studied in detail and used as drugs for passive immunotherapy or treatment of HIV (see further below). Heterogeneous human serum Abs cannot be used for this purpose; they are available in limited quantities, are different in each individual, and are composed of complex mixtures of antibodies, including blocking and virus-enhancing antibodies. The immortalized cell lines of the invention also allow one to isolate all or a portion of the expressed genes coding for the human mAb. These genes may be altered so as to produce a human mAb with even greater affinity for antigen and/or to change the isotype, idiotype, or effector functions of the human mAb. Expression systems have been developed to allow expression and secretion of genetically engineered human mAbs in mouse cells.

Generally, for therapeutic use of human mAbs to be most effective in HIV-infected individuals, the neutralizing human mAb(s) should be extremely potent, so that neutralizing concentrations can be attained in vivo following administration of milligram amounts of human mAb(s). It has been estimated that between 0.03 to 3 mg/ml of a neutralizing Ab with similar affinity to that of CD4-gp120 would be required to eliminate HIV infection in vivo (Layne et al. 1989). This would necessitate administration of approximately 0.15 to 15 g of Ab per patient, the higher ranges of which are not feasible because of the side-effects associated with administering such high protein doses and the difficulties and cost of producing such large amounts of purified antibodies. The affinity of our human mAb 1125H for gp120, however, is greater than that of CD4. The synergism which we have observed makes it possible to greatly reduce the concentration of human mAb. Without wishing to be bound by any theory, we believe that a dose reduction index of at least 1–2 orders of magnitude (10–100 fold) is achieved using the invention. Thus, the combination of synergistically neutralizing human mAbs of the invention allows more practical application of passive immunotherapy or treatment of HIV-infected individuals.

A potential problem with the use of human mAb therapy against HIV is the possible selection of viral mutants escaping neutralization. We believe that the problem is significantly diminished by the combined use of human mAbs according to the invention rather than use of a single human mAb, since two or more independent mutations would then be required to alter both the CD4 binding site and V-3 loop regions so that they are not recognized by either neutralizing human mAb.

The invention includes combinations of human mAbs against the CD-4 binding site region and the V-3 loop region which synergistically neutralize HIV-1. In order to determine which antibodies from these regions synergistically react, human monoclonal antibodies against each of these epitope clusters which have been produced, for example by the methods described below, are screened.

A given combination of a human monoclonal antibody against the CD-4 binding site and a human monoclonal antibody against the V-3 region can be screened in a standard neutralization assay for synergistic neutralizing activity by comparing the individual neutralizing activity of each antibody, with the neutralization activity in an assay with the antibodies combined. Examples of such neutralization assays are described below. The ability of the antibody combination to synergize will be evidenced by a significant increase in neutralization activity over that obtained in the presence of equivalent concentrations of the individual antibodies. The extent of synergy can be quantitated by calculating the Combination Index using know statistical methods.

For example, a given anti CD-4 binding site human monoclonal antibody can be screened for a significantly increased neutralization activity in combination with the 4117C antibody.

Similarly, a given anti V-3 human monoclonal antibody can be screened for synergistic activity by combining it with the 1125H antibody and testing neutralization activity in the same manner.

Another manner in which to obtain the synergistic antibodies of the invention is to screen human monoclonal antibodies against the CD-4 binding site region which competitively inhibit the binding of 1125H to gp120 in vitro, in combination with either 4117C, or antibodies which competitively inhibit the binding of 4117C to gp120 in vitro.

The antibodies employed in the combination of the invention are directed against the same epitope clusters as 1125H and 4117H. We have determined, however, that human monoclonal antibodies against other epitopes within these specific epitope clusters, i.e. the CD4 binding site epitope cluster and V-3 loop cluster, also synergistically react. For example, we have found at least one other antibody against the CD-4 binding site which synergistically reacts with 4117C but which is directed at an epitope within the CD-4 binding site cluster different from that of 1125H. This antibody, designated 5145A, is described below.

Figure 6:
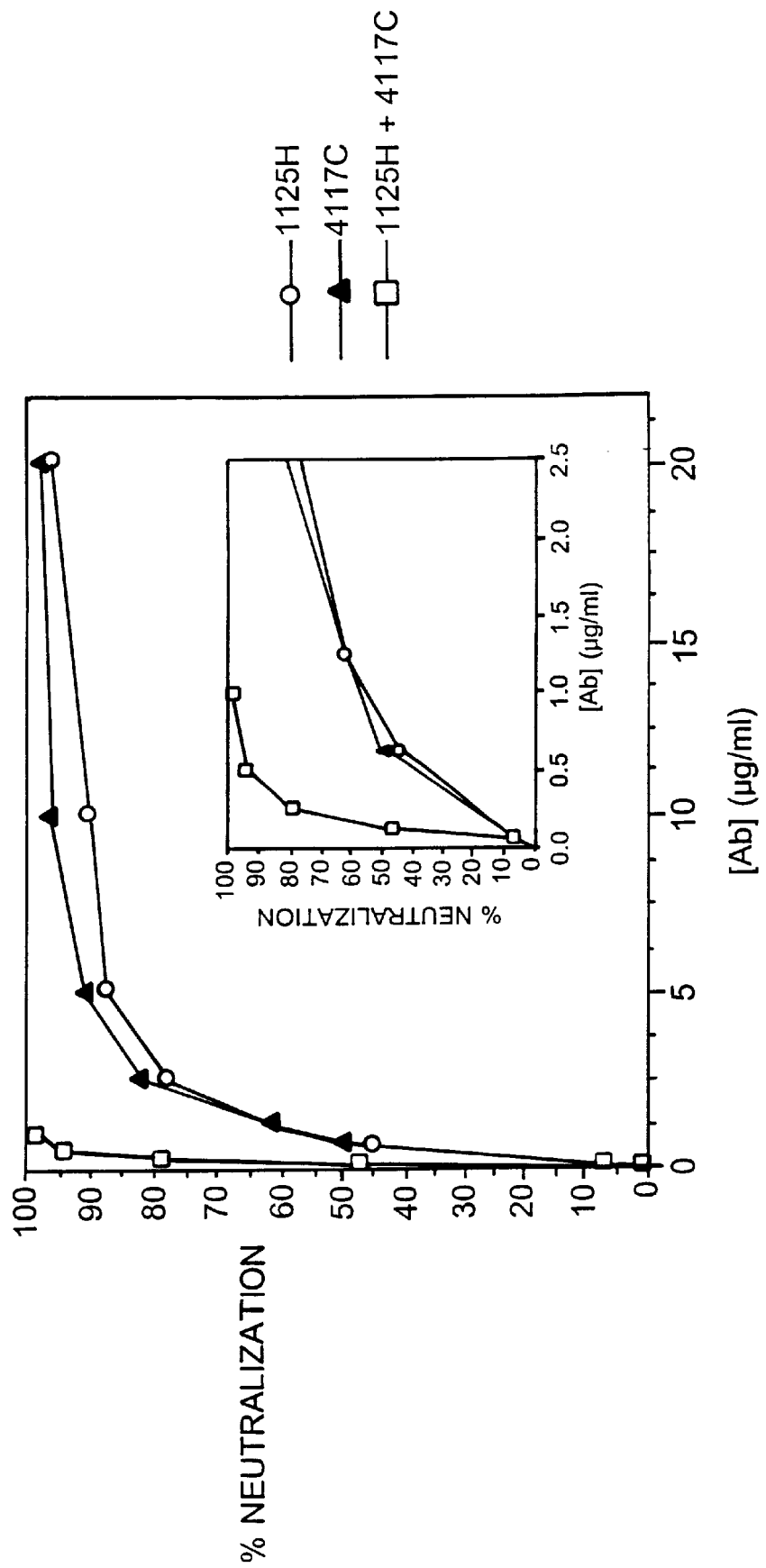
FIG. 6 depicts the synergistic neutralization of the MN strain by human mAbs 1125H and 4117C.

Significant synergistic values within the scope of the invention are, for example, those demonstrated for the results shown in FIGS. 6 and 7. Similarly, combination index values obtained for those results demonstrate significant synergism within the scope of the invention. Combination index values as a a measure of synergism are further discussed below.

Preferably the synergistic combination of human mAbs achieves 95% neutralization of about $1 \times 10^4$ infectious units of the MN strain of HIV-1 at a concentration of about 0.5 micrograms/ml.

In a preferred embodiment of the combination, one of the human mAbs which competitively inhibits the in vitro binding of antibodies produced by the cell line 1125H to gp120 combines synergistically in neutralizing HIV-1 with other human mAbs competitively inhibit the in vitro binding of antibodies produced by the cell line 4117C to gp120. In vitro competitive binding assays are well known in the art.

Another embodiment of the invention includes a combination of human mAbs wherein one of the human mAbs substantially has the epitope specificity of antibodies produced by the cell line 1125H and the other human mabs substantially have the epitope specificity of antibodies produced by the cell line 4117C. Means of determining epitope specificity are also well known in the art.

In another preferred embodiment, one of the human mAbs has the identifying characteristics of those obtained from the cell line 1125H and the other has the identifying characteristics of those obtained from the cell line 4117C.

Also included in the invention are transformed cell lines which produce human monoclonal antibodies which have the epitope specificity of those antibodies produced by the cell line 4117C.

Human monoclonal antibodies having these specificities are also included in the invention.

As noted above, polyclonal antibodies from different sources may be employed, in addition to the human antibodies we have described. Methods have been described in the literature for inducing neutralizing antibodies against different epitopes of HIV gp120 in both rodents and chimpanzees. Antibodies against the V3 loop have been induced in both rodents (Javaherian et al, 1990) and chimps (Girard et al., 1991) by immunizing animals with synthetic V3 peptides either in free form, or conjugated to KLH. Anti-V3 antibodies have also been induced by immunizing chimps with purified gp120 and gp160 (Berman et al., 1990). Antibodies against both regions can also be produced in chimpanzees which have been infected with HIV, although the V3 region is immunodominant, and anti-V3 antibodies will predominate over anti-CD4 binding site antibodies. Monoclonal antibodies against these gp120 epitopes can be prepared from immunized mice by standard techniques, and monoclonal antibodies can be prepared from chimps by following the EBV-transformation procedure described herein for human cells.

Specific antibodies against both the V3 region and against the CD4-binding site can be purified by immunoaffinity chromatography. In one example, AH-Sepharose beads are activated by treatment with glutaraldehyde, and conjugated to either purified V3 peptide or purified gp120. Antibodies against V3 can be obtained by passing 10-fold diluted hyperimmune serum through the columns to allow the antibodies to bind, and washing off unbound antibodies with saline and 0.5M NaCl solutions. V3-specific antibodies can be eluted from the V3 column by washing with tris-glycine buffer, pH2.7 while V3 specific antibodies can be eluted form the gp120 column by passing through excess V3 peptide. Antibodies against the CD4-binding site can be eluted from the gp120 column with tris-glycine buffer, and then purified by passing over a second gp120-affinity column in which the CD4-binding site had been blocked with excess soluble CD4. Under these conditions, the anti-CD4 binding site antibodies will not bind to the column and will be found in the flow-through, while all other antibodies will be retained.

The present invention also includes test kits to measure the presence of human Abs against the epitope[s] of the MAbs claimed in this application. The kits contain human monoclonal antibodies having the specificity described above, a solid phase on which is coated an antigen which the monoclonal antibodies are specific for, and means for detecting the formation of a complex between the monoclonal antibodies and the antigen. A competitive ELISA using biotin labeled human mAbs can be performed similarly to the competitive inhibition assay described below. Such an assay determines whether the sample has any antibody competing with the antibodies of the invention. An assay for determining the presence of the antigen which the mAbs of the invention bind to can also be performed using, for example, a sandwich format wherein a solid phase is coated with antibody to HIV envelope, the sample is added, and then biotin labeled mAb of the invention is added. Following a wash, enzyme labeled avidin would then be added as well as enzyme substrate. Such general types of assays are well known in the art.

The invention also includes kits for determining an antigen for which the MAbs of the invention are specific. For example such a kit may comprise the MAbs of the invention, a solid phase on which is coated an antibody specific for HIV-1 env, and means for detecting the formation of a complex among the MAbs of the invention, the antibody specific for HIV-1 env, and an HIV antigen for which the MAbs are specific. The practice of such a sandwich type immunoassay is well known to one skilled in the art.

Following is a description of how human monoclonal antibodies to CD-4 binding site and to the V-3 loop can be obtained.

Peripheral blood from HIV-1-seropositive individuals was used to establish transformed clonal human B cell lines which synthesize high affinity human mabs against HIV-1 envelope proteins. The HIV-1-seropositive donors had normal white blood cell counts and no history of opportunistic infections. Human mAbs obtained against the CD-4 binding site were found which are specific for divergent strains of HIV-1, including the IIIB, MN, SF-2 and RF strains. Three cell lines obtained which produce mAbs having this capability are referred to herein as 2173C, 2154B.1 and 1125H. These were deposited with the American Type Culture Collection, 12301 Parklawn Drive, Rockville, Md., 20852 on Oct. 16, 1990 and assigned accession nos. CRL10580, CRL10581, and CRL10582 respectively.

Also obtained was a human mAb against the V-3 region, 4117C, which reacts with less strain specificity than prior human antibodies against V-3. This mAb is specific for a variety of strains, including MN, SF-2 and other strains described below. Cell line 4117C was deposited with the American Type Culture Coll-ection, 12301 Parklawn Drive, Rockville, Md., 20852 on Jun. 11, 1991 and has been assigned accession number CRL 10770.

These cultures have been deposited to exemplify the invention, but procedures are described in detail below to allow one skilled in the art to obtain such materials. KAbs from the deposited cell lines can be used to aid in screening to identify cell lines producing mAbs specific for the same, or nearby, epitopes. Using procedures described in detail below, cell lines expressing these mAbs are obtained.

The term "neutralizing", where not otherwise defined, is used herein to mean the ability of antibodies, at a concentration no greater than approximately 100 $\mu$g/ml, to reduce in vitro infection of H9 cells by at least 90% (compared to control cultures to which no antibody is added) by HIV-1 in the range of $10^4$–$10^5$ total infectious units as assessed by the overnight neutralization assay described below.

Peripheral blood mononuclear cells from HIV infected individuals were immortalized by transformation with Epstein-Barr virus using a modification described below of the procedure of Gorny et al. [Gorny, M. K., V. Gianakakos, S. Sharpe, and S. Zolla-Pazner. (1989) Proc. Natl. Acad. Sci. USA 86:1624–1628]. The anti-CD4 binding site humab cultures were obtained by screening immortalized cultures for production of anti-env antibody using recombinant gp160 coated ELISA plates. Our use of recombinantly produced gp160 in screening differs from other researchers, who have used for example, HIV-1 lysate [Gorny, M. K., V. Gianakakos, S. Sharpe, and S. Zolla-Pasner. (1989) Proc. Natl. Acad. Sci. USA 86:1624–1628], fixed HIV-1-infected cells [Robinson, J. E., D. Holton, S. Pacheco-Morell, J. Liu, and H. McMurdo. (1990) AIDS 4:11–19; Posner, M., M. Mukherjee, T. Hideshima, T. C. Cannon, and K. Mayer (Jun. 20–24, 1990, San Francisco) Sixth International Conference on AIDS, 153], or ConA-immobilized glycoproteins from detergent-disrupted supernatants of HIV-1-infected cells [Robinson, J. E., D. Holton, S. Pacheco-Morell, and H. McMurdo. (1990) AIDS 4:11–19] to screen cultures. We prefer recombinant gp160 which is obtained from higher eukaryotic transformed hosts. For example, we used gp160 expressed by transformed baby hamster kidney cells as per Kieny et al. [Kieny, M. P., R. Lathe, Y. Riviere, K. Dott, D. Schmitt, M. Girard, L. Montagnier, and J. Lecocq. (1988) Protein Engineering 2:219–225] This version of gp160, supplied by Pasteur Merieux, lacks the site which is normally cleaved to form gp120 and gp41. The deletion of this cleavage site, however, is not believed to have any effect on the screening process and to be distant from the epitopet[s] which the antibodies of this invention are specific for. Alternative preferred sources include gp160 or gp120 obtained from other transformed higher eukaryotic hosts. For example, recombinant gp120 per Leonard et al. [Leonard, C. K., M. W. Spellman, L. Riddle, J. N. Thomas, and T. J. Gregory. (1990) J. Biol. Chem. 265:10373–10382] and recombinant gp120 ([Celltech, Inc.) available through the AIDS Research and Reference Reagent Program (NIH) are also believed effective in screening cultures for mabs of the invention.

Competitive ELISAs, testing for competitive inhibition with CD-4 can be performed in order to further screen for cultures producing anti-CD4 binding site humabs. Immunofluorescence and neutralization assays may be conducted in order to positively identify those antiCD-4 binding site cultures which are specific for the epitope which affords broad neutralizing activity across the four strains: IIIB, MN, SF-2 and RF, among others. In addition, peptides which present the hvl-V3 loop and peptides which present gp41 epitopes can be used as negative controls to establish the specificity of mAbs for the epitope[s] defined by the anti-CD4 binding site mAbs of this invention. These peptides are described in greater detail later.

Further screening to determine whether cultures are producing mAbs to the same epitope cluster as one of the antibodies of the invention can be done with a competitive ELISA assay using any of the three anti CD-4 binding site antibodies or anti V3 mabs which we have deposited. Such an assay would determine if mAbs from the culture being screened compete with those described herein in binding to an epitope presented on, for example, recombinant gp160 coated ELISA plates. MAbs which compete would be specific for the same or adjacent epitopes. A suitable competitive assay is described below.

The anti-CD-4 binding site mAbs of this invention do not react with LAV-2. Each of these types of mabs from our deposited cell lines reacted with both acetone and methanol-fixed HIV-1 infected cells. Furthermore, each also reacted with formaldehyde-fixed HIV-1 infected cells, a result obtained in our hands only when the epitope recognized is expressed on the infected cells' surface. We have also shown that all three antibodies from our deposited cell lines react with live HIV-1 infected cells.

To obtain antibodies against the V-3 region we substituted a peptide consisting of amino acids 305-328 of the MN strain for recombinant gp160 in screening. That sequence is Asn Tyr Asn Lys Arg Lys Arg Ile His Ile Gly Pro Gly Arg Ala Phe Tyr Thr Thr Lys Awn Ile Ile Gly Cys (SEQ ID NO:2), described in Gurgo C., Guo H. G., Franchini G., Aldovini A., Collatti E., Ferrell K., Wong-Staal F., Gallo R. G., Reitz M. S. Jr., Envelope Sequences of Two New United States HIV-1 Isolates, (1988) Virology 4164:531–536. 4117C may be characterized by its reactivity with the V3 peptide of the following strains: MN, SF-2, NY-5, CD451, WMJ-1, WMJ-3, Z-3, Z-321, and SC; and by its lack of reactivity with the following strains: WMJ-2, LAV-MA, BR, LAV-IIIB, PV-22, ELI, Z-6, NX3-3, JY-1, HXB-2 and MAL.

Figure 3:
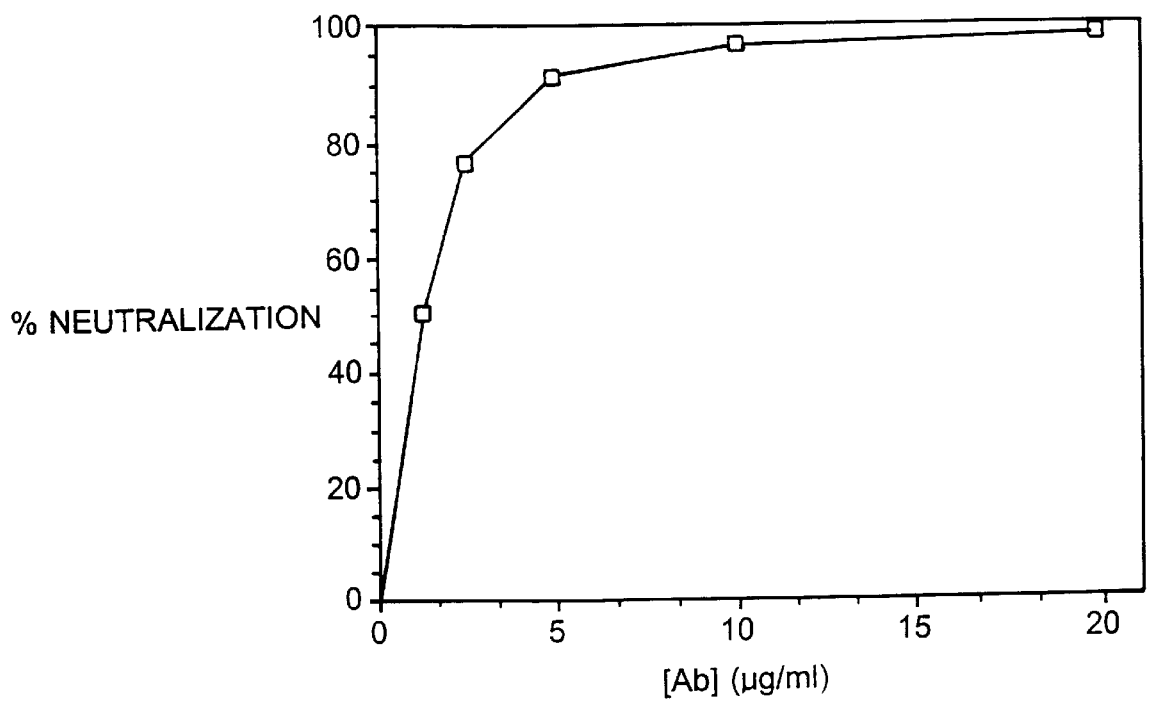
FIG. 3 is a graph depicting the neutralizing activity of mAb 1125H against the MN HIV-1 strain.

Similarly to the methods described above, competition assays with the deposited antibody 4117C may be carried out to further screen for related antibodies. Examination of the reactivity of antibodies against specific peptides can be used to determine the strain specificity of the screened antibodies. The neutralization abilities of the antibodies deposited have been determined, as described below. It should be appreciated that we used greater amounts of virus in the overnight neutralization assay than other investigators do in their neutralization assays that typically require as long as a week to detect viral infection of control cultures (i.e., those with no antibody added) [Ho, D. D., M. G. Sarngadharan, H. S. Hirsch, R. T. Schooley, T. R. Rota, R. C. Kennedy, T. C. Chanh, and V. L. Sato. (1987) J. Virol. 61:2024–2028]. Therefore, larger amounts of mAb are required to effect a given level of neutralization in our assay than in those assays in which many-fold less virus is added. To compare the efficacy of neutralization by our mAbs with those of other mabs whose neutralization activity is determined by several-day assays, it is necessary to compare the input number of tissue culture infectious units of virus utilized in the different studies. (A tissue culture infectious unit is approximately equal to two 50% tissue culture infectious doses (TCID) for HIV-1 grown in H9 cells [Harada, S., Y. Koyanagi, and N. Yamamoto (1985) Science 229:563–566]. Based on a comparison of this type, and our observation that the 1125H mAb neutralizes the MN (see. FIG. 3), and IIIB strains with approximately equal efficiency, we estimate that our Mabs neutralize some, if not most, strains of HIV-1 more efficiently than does the N70-1.5e mAb of Robinson, et al. [Robinson, J. E., D. Holton, S. Pacheco-Morell, J. Liu, and H. McMurdo (1990) AIDS Res. Human Retroviruses 6:567–579; Ho, D. D., XL Li, E. S. Daar, T. Moudgil, N. C. Sun, D. Holton, and J. E. Robinson (Jun. 20–24, 1990, San Francisco) Sixth International Conference on AIDS, 153] or the F105 mAb of Posner et al. [Posner, M., M. Mukherjee, T. Hideshima, T. C. Cannon, and K. Mayer (Jun. 20–24, 1990, San Francisco Sixth International Conference on AIDS, 153]. The 4117C mAb has approximately equal ability to neutralize to MN strain as does 1125H, and appears to neutralize SF-2 even better. These findings are particularly significant as MN and SF-2 are two of the most commonly rpresented strains in the United States.

Experiments were performed to determine which of our antibodies bound at or near the CD4 binding site of gp120. This putative site, shown by Lasky et al. [Lasky, L. A., G. Nakamura, D. H. Smith, C. Fennie, C. Shimasaki, E. Patzer, P. Berman, T. Gregory, and D. J. Capon. (1987) Cell 50:975–985] and other investigators to include gp120 amino acids 397–439 (using the amino acid numbering system for the HTLV-IIIB strain of HIV [Gallo, R., S.Salahuddin, M. Popovic, Q. Shearer, M. Kaplan, B. Haynes, T. Palker, R.

Redfield, J. Oleske, B. Safai, G. White, P. Foster, and P. Markham. (1984) Science 224:200–203]), is relatively conserved across HIV-1 strains. This was tested by conducting an experiment to determine whether soluble CD4 could inhibit the binding of the mAbs of our deposited cell lines to recombinant gp160 in a competitive ELISA assay. The results indicated that CD4 does indeed inhibit binding of the anti CD4 binding site human mabs to gp160 in a concentration-dependent manner.

FIG. 4 shows the apparent affinity constants of human anti-gp120 mAbs from the four deposited cell lines described. Antibodies with K-values in the vicinity of $10^9$ L/Mole [Berzofsky, J. A., S. L. Epstein, and I. J. Berkower. (1989) in Fundamental Immunology, Second Edition, W. E. Paul (ed.). Raven Press, Ltd., New York, p. 315–356] are considered to be of high affinity. By this standard, all four human mabs possess high affinity for gp120.

Further characterization of the anti-CD4 binding site human mabs, by way of Western blot analysis using strips prepared with HIV-1 lysate, shows that the epitopes of all 3 of these types of mAbs are destroyed by reduction of disulfide bonds. This indicates that their epitope[s] is dependent on the 3-dimensional conformation of gp120 and that it is unlikely that linear synthetic antigens which have been created by others [Lasky, L. A., G. Nakamura, D. H. Smith, C. Fennie, C. Shimasaki, E. Patzer, P. Berman, T. Gregory, and D. J. Capon (1987) Cell 50:975–985; Sun, N., D. D. Ho, C. R. Y. Sun, R. Liou, W. Gordon, M. S. C. Fung, X. Li, R. C. Ting, T. Lee, N. T. Chang, and T. Chang (1989) J. Virol. 63:3579–3585] contain the epitopes recognized by our mAbs. Rather, the epitope[s] of these mAbs is probably only recognized upon formation of the appropriate loop or loops by disulfide bonding. Antibody 4117C shows diminished reactivity with reduced gp120, as compared with unreduced gp120, but not complete loss of activity.

Isotype characterization of the four mabs of our deposited cell lines was determined by using a variation of the immunofluorescence assay for heavy chain analysis and a variation of ELISA for light chain analysis. The heavy chain isotypes, as determined by immunofluorescence assay, was found to be IgG1. The light chain isotype of the CD4 binding site antibodies was determined to be Kappa whereas that of the 4117C was determined to be lambda. The procedures are described below.

The nAbs of the present invention can be used therapeutically to treat HIV-1 infected individuals. They may be administered by themselves or in conjunction with other anti-viral therapies, such as AZT or DDI, in order to slow the progress of HIV-1 induced disease.

The synergistic combination which we have discovered is most exciting in this regard as much less of these antibodies is required in order to neutralize HIV. They provide a distinct advantage over the single human antibodies which have been described.

In order to administer the synergistic antibodies of the invention, combinations of purified HuMAbs, mixed in appropriate ratios, can be adjusted to 5% solution in sterile saline, yielding a concentration of 50 mg/ml. The best ratio of the synergizing antibodies is determined experimentally, using the 24 hour fluorescent focus assay described below. For example, equipotent concentrations of the two antibodies 1125H and 4117C can be used; i.e. a concentration of each which has been determined to give comparable levels of neutralization to each other. The amount of this solution required for protection can be determined in animal experiments, performed first in Hu-SCID mice (Mosier et al. 1988, McCune et al. 1988) and subsequently in chimpanzees. The therapeutic reagent can consist of as few as two synergizing antibodies, although it is believed that the most efficient composition will contain a larger number of different antibodies directed against the two major antigenic sites. This is in order to increase the crossreactivity of the antibodies to different HIV variants which may exist in patients, to inhibit the generation of escape mutants, and to decrease the likelihood of a deleterious anti-idiotype response.

It is believed that it may also be beneficial to mix engineered antibodies of different isotypes, including IgGs, IgMs, and IgAs, in order to increase the affinities and effector activities of the antibodies. It is also believed to be beneficial to include antibodies conjugated to toxins, mentioned below, to increase the killing of infected cells, and engineered bispecific antibodies, to increase targeting of infected cells to immune cell-mediated cytotoxic mechanisms.

Based on available data and theoretical considerations, a reasonable assumption is that to prevent virus spread in vivo would require achieving plasma concentrations of synergizing neutralizing antibody combinations of 1 to 30 ug/ml. 1–5 mls of the 5% solution (50–250 mg total Ig) is given by intravenous injection to patients. Assuming a total blood volume of 5L, and assuming that all of the delivered Ig remains in the plasma with a half life of 2 weeks, this should result in an initial plasma concentration of the HuMAbs ranging from 10–50 ug/ml. To maintain this level would then require biweekly to bimonthly injections. The treatment is administered to inhibit viral spread, although it may lead to reduction or eradication of virus infection by immunocytoxicity mechanisms after a reasonable period of treatment.

Passive administration of human mAbs of the invention may also be used to prevent HIV-1 infection in cases of acute exposure to HIV. As noted above, studies indicate [Devash, Y., T. A. Calvelli, D. G. Wood, K. J. Reagan, and A. Rubinstein. (1990) Proc. Natl. Acad. Sci. USA 87:3445–3449] a striking correlation between the presence of high affinity serum Abs against the hvl-V3 region of the MN strain in human neonates born to HIV-1 seropositive mothers and the absence of HIV-1 infection in the neonates. Therefore, it can be concluded that the HIV-1 seropositive mother transfers high affinity anti-hvl-v3 antibodies to her fetus, and the fetus is thus protected from HIV-1 that it may receive from the mother at the time of birth. The results of Devash are evidence that high affinity neutralizing Ab against HIV-1 can protect the fetus from HIV-1 infection when present at the time of viral challenge. Hence, the HIV-1 neutralizing mAbs of this invention could be passively administered to pregnant seropositive women to prevent their fetuses from becoming HIV-1 infected.

In addition, these combinations of mAbs may be used to prevent HIV-1 infection by administering them to individuals near the time of their exposure to HIV-1. Properties of the preferred mAbs of this invention which make them excellent even by themselves for these applications are: 1) their demonstrated HIV-1 neutralizing activity in vitro at low mAb concentrations, 2) their broad HIV-1 strain specificity, 3) their high affinity for antigen (HIV-1 gp120), 4) the fact that they are of human origin and will, therefore, elicit few, if any, deleterious immune reactions when administered to humans, and 5) the heavy chain isotype of the mabs is IgG1, which is significant because human IgGAbs are the only class of Ab able to cross the placenta, and Abs of the IgG1 subclass can potentially kill HIV-1-infected cells in vivo via Ab- and complement-dependent cytotoxicity (ACC) and/or Ab-dependent cellular cytotoxicity (ADCC) (see further below).

Although the mAbs of this invention by themselves can be used to prevent HIV-1 infection, the mabs may be modified to enhance their in vivo anti-viral activity by covalent attachment of a toxin such as ricin A or pokeweed antiviral protein to the mabs. It has been demonstrated that such anti-HIV-1 mAbs-toxins (immunotoxins) are capable of specifically killing HIV-1 infected cells in vitro. In considering the use of these Mabs to prevent HIV-1 infection, the killing of HIV-1 infected cells via ACC, ADCC, or following mAb conjugation with a toxin, could complement the neutralizing activity of our mabs by eliminating a very small percentage of HIV-1 infected cells which might result if 100% neutralization of HIV-1 by the mabs is not obtained.

Gram quantities of this invention's mAbs are preferably obtained in order to administer efficacious amounts of these reagents to humans in-vivo. These amounts could be obtained by growth of our human cell lines in a mini-bioreactor. Additionally, cost-effective methods to increase human mAb production are: 1) fusion of our EBV-transformed lines with a human/mouse heteromyeloma [Teng, N. N. H., K. S. Lam, F. C. Riera, and H. S. Kaplan. (1983) Proc. Natl. Acad. Sci. USA 80:7306–7312; Kozbor, D., A. E. Lagarde, and J. C. Roder. (1982) Proc. Natl. Acad. Sci. USA 79:6651–6655] and 2) PCR amplification of expressed immunoglobulin $V_H$ and $V_L$ genes from human cell lines using published human primer sequences [Larrick, J. W., L. Danielsson, C. A. Brenner, E. F. Wallace, M. Abrahamson, K. E. Fry, and C. A. K. Borrebaeck. (1989) Biotechnology 7:934–938], followed by cloning of these genes into available eukaryotic expression vectors containing human constant region genes. [Orlandi, R., D. H. Gussow, P. T. Jones, and G. Winter. (1989) Proc. Natl. Acad. Sci. USA 86:3833–3837]. Alternatively the genes could be directly cloned from cDNAs or genomic DNA of the antibody producing human or non-human cells. The latter constructs are then expressed as mabs at high levels in mouse myeloma cell lines. Transformed cell lines producing recombinant monoclonal antibodies are included within the scope of the invention, as are the antibodies produced thereby.

The invention also includes moieties having the same function as monoclonal antibodies, such as Fab fragments, $F(ab')_2$, Fd or other fragments, modified proteins such as chimeras with altered Fc regions, or having mutagenized idiotypic regions, so long as they bind to the same epitope as the human monoclonal antibodies of the invention. Techniques for producing such fragments or modified antibodies are known to one skilled in the art [Parham, P. (1986) In Cellular Immunology 4th Ed. (ed. D. M Weir), vol. 1, chap. 14. Blackwell Scientific Publications, California].

Previous studies have shown that the affinities of humabs to their antigens, and the abilities of these antibodies to neutralize infectious agents can be significantly enhanced by changing their isotypes. For example, a human IgG mAb against group B streptococci was converted to an IgM by standard recombinant DNA methods (Shuford et al. 1991). The IgM form of the antibody showed an approximately 100-fold greater level of binding in an ELISA assay than the IgG, and was able to prevent mice from lethal effects of the bacteria at a greater than 16 fold reduction in concentration.

Significant enhancement of the neutralizing activity of antibodies described herein against either the V3 or anti-CD4 epitope clusters can be expected to be achieved by changing their isotypes. It is believed that the preferred therapeutic reagent of this invention consists of mixtures of engineered antibodies of different isotypes, including IgGs, IgMs, and IgAs, in order to increase the affinities and effector activities of the antibodies.

The present invention is further described herein below. These examples are for illustration and are not intended to limit the invention.

EXAMPLES

Peripheral blood from HIV-1 seropositive individuals who are hemophiliacs was obtained. These individuals were classified as Walter Reed Stage 2A, i.e., they had normal white blood cell counts and no history of opportunistic infections.

Preparation and screening of cell lines producing human mabs according to this invention Peripheral blood mononuclear cells were isolated by centrifugation of fresh, heparinized blood, diluted 1:3 with RPMI1640 medium (Flow®), on Histopaque (Sigma®) at 400×g for 30 min. at room temperature. Cells at the medium/Histopaque interface were recovered and diluted 7–8 fold with RPMI 1640 medium. The cells were spun down (400×g, 20 min.), and then resuspended in 50 ml of RPMI 1640 medium, counted, and spun down again as before. Cells were then resuspended at a density of $2\times10^6$ cells/ml in RPMI 1640 medium supplemented with 15% (vol/vol) fetal calf serum (HyClone®), 2 mM L-glutamine, penicillin (50 units/ml), and streptomycin (50 $\mu$g/ml) (complete medium). Epstein-Barr virus (EBV) 100× stock, [Raubitschek, A. A. (1985) in Human Hybridomas and Monoclonal Antibodies, E. G. Engleman, S. K. H. Foung, J. Larrick, and A. Raubitschek (ed.). Plenum Press, New York, P. 454–455] was then added so that it constituted 1⁄10 of the final volume of the cell suspension, and the cells were incubated overnight at 37° C. in 5% $CO_2$ in a 25 $cm^2$ flask. The following day, the cells were gently resuspended, diluted approximately 10-fold with RPMI 1640 medium, and spun down. The pellet was resuspended at a final density of $10^4$ cells/ml in complete medium. The cells were then plated in U bottom 96-well plates at 100 $\mu$l (1000 cells) per well onto 100 $\mu$l of irradiated (3500 rads) rat embryo fibroblasts in complete medium. The cultures were fed weekly for 4 weeks at which time approximately 45% of the wells exhibited growth. Then their supernatants were assayed for anti-env Ab production (see below). Those cultures testing positive were picked onto fresh irradiated rat embryo fibroblasts in 96-well plates and re-assayed the following week. Cultures remaining positive were then sublined onto irradiated rat embryo fibroblasts at densities ranging from 1 to 100 cells/well. Those cultures growing in plates in which the number of wells with growth indicated >95% probability of monoclonality as determined by the Poisson distribution (Coller, H. A., and B. S. Coller. (1987) in Methods of Hybridoma Formation, A. H. Bartal, and Y. Hirshaut (ed.). Humana Press, Clifton, N.J., p. 231–236) were re-tested for anti-envelope antibody production, and those testing positive were expanded into bulk culture. In this way we obtained cell lines 1125H, 2154B.1, 2173C and 4117C. The monoclonality of these cultures was confirmed by Southern blot analysis using an immunoglobulin $J_H$ gene probe.

Southern blot analysis to determine clonality of cell lines.

DNA was isolated from the four identified cell lines followed by restriction enzyme digestion, agarose gel electrophoresis, blotting to nitrocellulose, and hybridization to $^{32}P$-labeled nick-translated probe. [Eckhardt, L. A., S. A. Tilley, R. B. Lang, K. B. Marcu, and B. K. Birshtein. (1982) Proc. Natl. Acad. Sci. USA 79:3006–3010]. The DNA was cut with Hind III, which allows visualization of rearrangements due to V-D-J joining upon hybridization with an immunoglobulin $J_H$ region probe [Ravetch, J. V., U. Siebenlist, S. Korsmeyer, T. Waldmann, and P. Leder. (1981) Cell 27:583–591]. The $J_H$ probe used was a EcoRI-HindIII fragment approximately 3.3 kilobases in length from the germ line $J_H$ locus; the HindIII site at its 3' end is present in the germ line DNA [Ravetch, J. V., U. Siebenlist, S. Korsmeyer, T. Waldmann, and P. Leder. (1981) Cell 27:583–591], whereas the EcoRI site at its 5' end was created upon cloning. The monoclonality of the four cell lines was confirmed.

Methods Used for Detection of Human Anti-gp120 mAbs Produced by Human Cell Lines ELISA assays were used to detect HIV env-specific Abs. The initial screening of EBV-transformed human cultures for production of anti-env Ab was done using either recombinant gp160 [Kieny, M. P., R. Lathe, Y. Riviere, K. Dott, D. Schmitt, M. Girard, L. Montagnier, and J. Lecocq. (1988) Protein Engineering 2:219–225] or $V3_{MN}$ peptide to coat PVC ELISA plates (Flow/ICN). In later assays on supernatants from cultures identified as positive in the initial screening, a variety of other HIV proteins or peptides can be used to determine the specificity of the human mAbs. These include recombinant gp120 of the IIIB strain produced by Celltech, Inc. and available through the AIDS Research and Reference Reagent Program (NIH) or described by [Leonard, C. K., M. W. Spellman, L. Riddle, J. N. Thomas, and T. J. Gregory. (1990) J. Biol. Chem. 265:10373–10382]; synthetic V3 peptides from a variety of strains (strain specificity is described above); or p121, a gp41 peptide (amino acids 565–646) sold commercially by Dupont or described in Chang, et al., European Patent Application 0199438 published Oct. 29, 1986. 4117C is negative for gp120 of the IIIB strain and for p121. 1125H is negative for the V3 peptides, and for the gp41 peptide as well. Unless noted otherwise, 50 ng/well of protein diluted in $Na_2CO_3$/ $NaHCO_3$ buffer, pH 9.8 was incubated in the plates overnight at 4° C. The following day, the plate was washed 3 times with PBS/tween/azide (Sigma® PBS with 0.05% Tween 20, 1 mM $NaN_3$). Next, the wells of the plate were blocked (to prevent nonspecific binding) by incubation with 50 $\mu$l of 2% BSA in PBS for 1.5 hr., 37° C. After washing as before, 50 $\mu$l of supernatant from human cell lines was added to the wells and incubated for 1.5 hr., 37° C. Unbound Ab was washed from the wells, and 50 $\mu$l of a 1/500 dilution of goat anti-human IgG conjugated to alkaline phosphatase (Zymed®) in 2% BSA was added to each well. After an incubation and wash identical to those discussed above, 50 $\mu$l of alkaline phosphatase substrate (disodium p-nitrophenyl phosphate), 1 mg/ml in diethanolamine buffer (1M diethanolamine, 0.5 mM $MgCl_2$, 3 mM $NaN_3$, pH 9.8) was added. The absorbance at 405 nm was read in a Titertek Multiskan Pluss ELISA reader (Flow®) at times ranging from 5 min. to 2 hr. following substrate addition. The background obtained when culture media was used rather than supernatant from human cell lines was automatically subtracted from the results by the ELISA reader.

Radioimmunoprecipitation and Western Blot Assays.

For radioimmunoprecipitation assays, glycoproteins in HIV-1-infected cells at $5-7 \times 10^5$ cells/ml were labeled with $^3$H-glucosamine (100 $\mu$Ci/ml) as described [Pinter, A., W. J. Honnen, S. A. Tilley, C. Bona, H. Zaghouani, M. K. Gorny, and S. Zolla-Pazner. (1989) J. Virol. 63:2674–2679]. The cells were then lysed and immunoprecipitated as previously described [Pinter, A., and W. J. Honnen. (1988) J. Virology 62:1016–1021]. Briefly, the cell pellet was brought up in lysis buffer at a concentration of $5 \times 10^6$ cells per ml. The lysate was then precleared with fixed, killed staphylococcus aureus cells (Staph A), and 70 $\mu$l of pre-cleared lysate was added to 70 $\mu$l of supernatant from human Ab-producing cell lines or 1/400 dilution of human sera. Following an incubation and precipitation by Staph A, the pellet was brought up in Laemmli sample buffer containing 1% DTT and run on an 11% polyacrylamide gel as described [Laemmli, U. K. (1970) Nature 227:680–683]. Fluorography [Bonner, W. M., and R. A. Laskey. (1974) Eur. J. Biochem. 46:83–88] then allowed detection of radiolabeled, immunoprecipitated glycoproteins in the gel.

Western blot analysis was performed using strips prepared with HIV-1 lysate essentially as described [Pinter, A., W. J. Honnen, S. A. Tilley, C. Bona, H. Zaghouani, M. K. Gorny, and S. Zolla-Pazner. (1989) J. Virol. 63:2674–2679]. The lysate was diluted in buffer composed of 0.01M Tris hydrochloride (pH 7.4), 10% glycerol, 0.01% bromophenol blue, either 0 or 1% DTT, and 1% SDS. The Western blot strips were incubated with a ½ dilution of supernatant from human Ab-producing cell lines or a 1/100 dilution of human serum, and bound Ab was detected as described [Pinter, A., W. J. Honnen, S. A. Tilley, C. Bona, H. Zaghouani, M. K. Gorny, and S. Zolla-Pazner. (1989) J. Virol. 63:2674–2679].

HIV Strains

HIV-1 strains IIIB [Popovic, M., M. G. Sarngadharan, E. Read, and R. C. Gallo. (1984) Science 224:497–500; Ratner, L., W. Haseltine, R. Patarca, K. J. Livak, B. Starcich, S. F. Josephs, E. R. Doran, J. A. Rafalski, E. A. Whitwhoen, K. Baumeister, L. Ivanoff, S. R. Petteway, M. L. Pearson, J. A. Lautenberger, T. S. Papas, J. Ghrayeb, N. T. Chang, R. C. Gallo, and F. Wong-Staal. (1985) Nature 313:277–284] and SF2 [Levy, J. A., A. D. Hoffman, S. N. Kramer, J. A. Landis, J. M. Shimabukuro, and L. S. Oshiro. (1984) Science 225:840–842; Sanchez-Pescador, R., M. D. Power, P. J. Barr, K. S. Steimer, M. M. Stempten, S. L. Brown-Shimer, W. W. Gee, A. Renard, A. Randolph, J. A. Levy, D. Dina, and P. A. Luciw. (1985) Science 227:484–492] were obtained from Dr. Jeffrey Laurence, Cornell University School of Medicine; strains MN [Gallo, R. C., S. Z. Salahuddin, M. Popovic, G. M. Shearer, M. Kaplan, B. Haynes, T. J. Palker, R. Redfield, J. Oleske, B. Safai, G. White, P. Foster, and P. 0. Markham. (1984) Science 224:500–503; Shaw, G. M., B. H. Hahn, S. K. Arya, J. E. Groopman, R. C. Gallo, and F. Wong-Staal. (1984) Science 226:1165–1171] and RF [Popovic, M., M. G. Sarngadharan, E. Read, and R. C. Gallo. (1984) Science 224:497–500; Starcich, B. R., B. H. Hahn, G. M. Shaw, P. D. McNeely, S. Modrow, H. Wolf, E. S. Parks, W. P. Parks, S. F. Josephs, R. C. Gallo, and F. Wong-Staal. (1986) Cell 45:637–648] were obtained from the NIH AIDS Research and Reagent Repository. The identities of strains IIIB, MN, and RF were confirmed by us using strain-specific antisera against the hypervariable V3 loop (hvl-v3) of each strain in an immunofluorescence assay. The IIIB-specific chimpanzee antiserum was obtained through a collaboration with Dr. Marc Girard, Pasteur Institute, whereas the MN- and RF-specific rabbit antisera were generously provided by Dr. Robert Neurath, New York Blood Center. An HIV-2 strain, LAV-2 [Clavel, F., D. Guetard, F. Brun-Vezinet, S. Chamaret, M. A. Rey, M. O. Santos-Ferreira, A. G. Laurent, C. Dauguet, C. Katlama, C. Rouzioux, D. Klatzmann, J. L. Champalimaud, and L. Montagnier. (1986) Science 233:343–346] was obtained from Dr. Alvin Friedman-Kien, New York University School of Medicine, with permission from Luc Montagnier, Pasteur Institute.

Immunofluorescence Assays for HIV Strain Specificity of mabs

Prior to attachment of cells to Multi-spot microscope slides (Shandon) for immunofluorescence analysis, the slides were treated with poly-L-lysine (100 µg/ml in PBS, 50 ml per well) for 30 min at room temperature. The slides were then washed with distilled water and dried. Cells that were 100% HIV-1-infected or uninfected were then washed in sterile PBS, resuspended in PBS at a density of $1-2\times10^6$ cells/ml, and incubated on the poly-L lysine-coated slides (50 µl cell suspension/well) at 37° C. for 30 min. The slides were then washed 2× in 100–200 ml PBS, using a slide-holder and trays. For formaldehyde fixation, 0.5% formaldehyde in PBS containing 10 mM $NaN_3$ was then added to each well of the slides and incubated with the immobilized cells for 30 min. at room temperature. The slides were then washed 1× in distilled $H_2O$ as discussed above and allowed to dry. For acetone or methanol fixation, following the 2 washes in PBS discussed above, the slides were washed 1× in distilled water and then incubated in 100–200 ml of acetone or methanol for 8 mins. The slides were then removed from the fixative and allowed to air dry.

Prior to addition of human Abs to the fixed cells on slides, non-specific binding was blocked by incubation of the slides with 1 mg/ml bovine gamma globulin in PBS for 30 min. at 37° C. After washing 2 times in PBS and once in distilled $H_2O$, the slides were allowed to air dry. Undiluted supernatant from human Ab-producing cell lines or serum diluted 1/100 to 1/200 in 1 mg/ml bovine gamma globulin in PBS was then incubated at 25–50 µl well for 1 hr. at 37° C. with the fixed cells on the slides. After washing and drying the slides as discussed above, a 1/50 dilution of goat anti-human IgG conjugated to FITC (Zymed) in 1 mg/ml bovine gamma globulin in PBS was incubated with the slides as in the previous step. After washing and air drying the slides as discussed above, the cells on the slides were counterstained with 0.05% Evans Blue for 10 min. at room temperature. The slides were then washed extensively with distilled $H_2O$ and air dried. Finally 2 µl per well of 0.033 M DTT in 50% glycerol in PBS was added as preservative, a coverslip was placed over the wells, and the slides were viewed under a Nikon Diaphot immunofluorescence microscope.

Determination of mAb Isotypes

Heavy chain subclass was determined using a variation of the immunofluorescence assay. Human mAb-producing cells were attached to slides and fixed with acetone. The slides were blocked with bovine gamma globulin and washed as discussed above. Next, a 1/5000 dilution of human IgG subclass-specific mouse monoclonal Ab (Zymed) (specifically, anti-IgG1 and anti-IgG2 were used in these experiments) was added and incubated for 1 hr. at 37° C. Following washing and drying of the slides, biotinylated goat antimouse IgG (Zymed), 1/200 dilution, was added and incubated for 1 hr., 37° C. After washing and drying the slides, a 1/50 dilution of FITC/streptavidin (Zymed), was added and incubated for 1 hr., 37° C. After washing and drying the slides, the cells were counterstained, and viewed as discussed above.

Light chain isotype was determined by a variation of the ELISA assay discussed above. Following incubation of supernatant from mAb-producing human cells with gp160 in duplicate ELISA wells, the mAb isotype was determined by development of one well with goat anti-human kappa Ab conjugated to alkaline phosphatase and the other well with goat anti-human lambda Ab conjugated to alkaline phosphatase. Both of the latter reagents (Tago) were used at 1/3250 dilution.

Competitive Inhibition Assays

These assays were done using a variation of the ELISA procedure discussed above. ELISA plates were coated with gp160, blocked with BSA, and washed. In the CD4 inhibition experiments, a constant volume of supernatant from human Ab-producing cells was added to varying amounts of soluble CD4 (in PBS) in eppendorf tubes, and RPMI was then added to yield a constant total volume. After mixing, the supernatant/CD4 mixtures were pipetted at 50 µl/well into the ELISA plates. The remainder of the ELISA procedure was carried out as discussed above.

Neutralization Assay

Prior to conducting neutralization assays, the human mAbs were purified on recombinant protein A Sepharose columns essentially as described [Harlow, E., and D. Lane. (1988) in Antibodies: A laboratory manual. Cold Spring Harbor Laboratory, Cold Spring Harbor, N.Y., p. 310]. The column fractions containing mAb (as determined by ELISA assay of fraction aliquots) were concentrated in an AMICON centriprep 30 column and dialyzed against PBS. An irrelevant mAb of the IgG2 subclass was purified in the same manner from the 1A2 cell line [Siadak, A. W., and M. E. Lostrom. (1985) in Human Hybridomas and Monoclonal Antibodies, E. G. Engleman, S. K. H. Foung, J. Larrick, and A. Raubitschek (ed.). Plenum Press, New York, p. 167–185], which was derived from the GM1500 cell line [Dolby, T. W., J. Devuono, and C. M. Croce. (1980) Proc. Natl. Acad. Sci. USA 77:6027–6031]. The purified 1A2 mAb was used as a negative control in neutralization and competitive inhibition experiments. The neutralization assay was carried out as follows. Purified Abs, or combinations of Abs, were diluted in complete media containing 10% FCS to obtain concentrations ranging from 0.1 to 20 µg/ml in a total volume of 100 µl. Included in this volume was approximately $10^4$–$10^5$ tissue culture infectious units of HIV-1. After a 30 min. preincubation of virus and mAb at room temperature, the mixtures were each added to $1\times10^5$ H9 cells in a final volume of 200 µl. Following an overnight incubation at 37° C., the cells in each well were plated onto separate wells of poly L-lysine-coated slides and stained sequentially with a rat anti-nef serum (1/200) followed by a rabbit anti-rat IgG Ab conjugated to FITC (1/50) (Zymed). The latter two antibodies were diluted in 1 mg/ml bovine gamma globulin in PBS. The cells were counterstained with Evan's Blue, and the percentage of infected cells from each culture relative to the control (no mAb added) was assessed by counting immunofluorescent cells versus total counterstained cells under the fluorescence microscope.

Specificity of mabs

Figure 1:
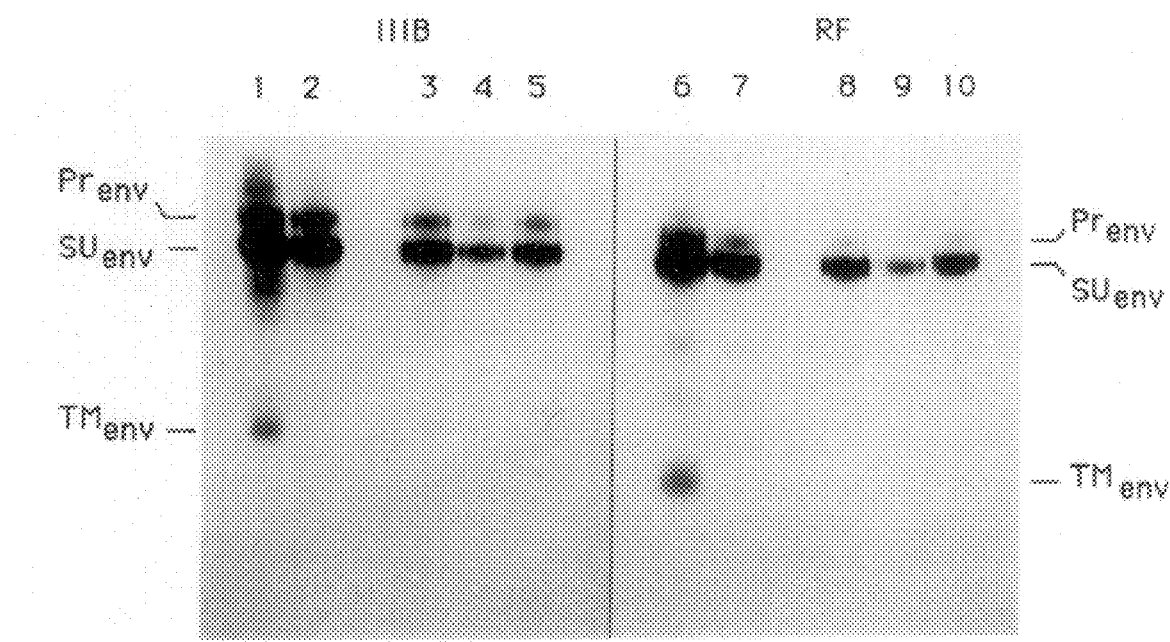
FIG. 1 depicts electrophoretic patterns of mAbs 1125H, 2173C, and 2154B.1 reacting with gp120 and gp160 on 11% polyacrylamide gels in SDS.

The specificity of 1125H, 2173C and 2154B.1 for gp120 was determined by ELISA reactivity of supernatants with recombinant gp120 as well as by radioimmunoprecipitation/SDS gel analysis using HIV-1 infected cell lysates. FIG. 1 shows the results. In the left panel (lanes 1–5), lysate from H9 cells infected with the IIIB strain was used, whereas in the right panel (lanes 6–10), lysate from H9 cells infected with the RF strain was used. These lysates were immunoprecipitated with: a 1/400 dilution of human serum from an HIV-1 seropositive individual (lanes 1 & 6); 0.7 µg purified 1125H mAb (lanes 2 & 7); undiluted supernatant from 1125H (lanes 3 & 8), 2154B.1 (lanes 4 & 9), and 2173C (lanes 5 & 10) cells. The latter three supernatants contained approximately 1–3 µg mAb/ml.

Results with the human serum (lane 1, positive control) show that the expected IIIB strain glycoproteins, gp160 ($Pr_{env}$, precursor envelope protein), gp120 ($SU_{env}$, surface envelope protein), and gp41 ($TM_{env}$, transmembrane envelope protein) are immunoprecitated. The corresponding glycoproteins of the RF strain (lane 6) each migrate at a lower apparent molecular weight than their counterparts from the IIIB strain (lane 1). This must be due to glycosylation differences in the RF and IIIB strain glycoproteins, since there is no significant difference in the number of amino acids in these molecules between RF and IIIB strains [Starcich, B. R., B. H. Hahn, G. M. Shaw, P. D. McNeely, S. Modrow, H. Wolf, E. S. Parks, W. P. Parks, S. F. Josephs, R. C. Gallo, and F. Wong-Staal (1986) Cell 45:637–648]. Since the names gp160, gp120, and gp41 given to the IIIB strain-related isolates of HIV-1 are only appropriate to glycoproteins migrating at the apparent molecular weights of 160, 120, and 41 kilodaltons, we have chosen to use the more appropriate names of $PR_{env}$, $SU_{env}$, and $TM_{env}$, which imply a specific protein structure and function for these molecules rather than an apparent molecular weight. Results with our nAbs (lanes 2–5 & 7–10) demonstrate that they are specific for $SU_{env}$ (gp120 of IIIB strain), reacting only with the $PR_{env}$, which contains the $SU_{env}$ sequences, and the $SU_{env}$ itself, but not with the $TM_{env}$ (gp41 of IIIB strain). Furthermore, the mAbs recognize both the RF and IIIB strain $SU_{env}$ molecules. Thus these human mabs are highly specific for gp120 and reactivity with both IIIB and RF glycoproteins is shown. The 4117C humAb is specific for gp120 as determined by ELISA and Western blot analyses.

Strain Specificity

The strain specificity of the 1125H, 2173C, 2154B.1 and 4117C mAbs was tested by immunofluorescence assay using fixed cells infected with one of several HIV strains.

The anti-CD4 mAbs were reactive with the IIIB, MN, SF-2 and RF HIV-1 strains, as well as with one (JRCSF) of two primary HIV isolates tested. None of these mAbs reacted with LAV-2, an HIV-2 isolate. Each of the three mAbs reacted with both acetone- and methanol-fixed HIV-infected cells. Furthermore, each of the mAbs reacted with formaldehyde-fixed HIV-1-infected cells, a result obtained in applicant's hands only when the epitope recognized by the mAb is expressed at the cell surface. Each of the mabs also reacted with live, HIV-1-infected cells.

The 4117 mAb was reactive with the MN, SF-2, and the JRCSF primary isolate, as well as with two strains known as FV and 11699, but not with the IIIB and RF strains.

CD4 Competition

To test whether the epitope recognized by the 1125H, 2173C and 2154B.1 mAbs is in or near the CD4 binding site of gp120, the ability of soluble CD4 to inhibit the binding of applicant's mAbs to recombinant gp160 in a competitive ELISA assay was examined.

Figure 2A:
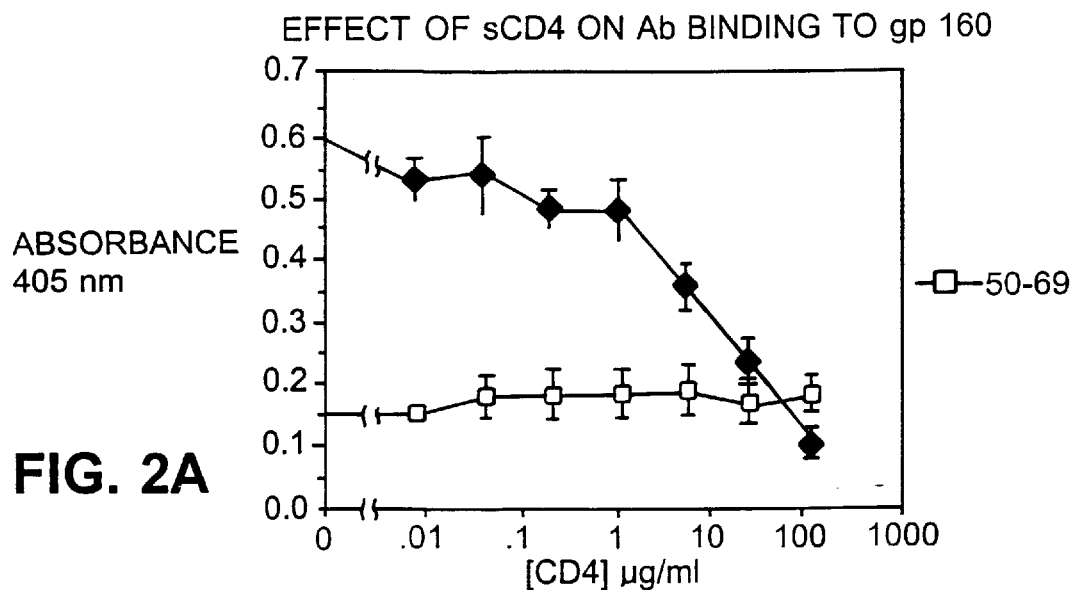
FIGS. 2A–2C are graphs depicting competition ELISA using a gp160 coated plate and a CD4 inhibitor.
Figure 2B:
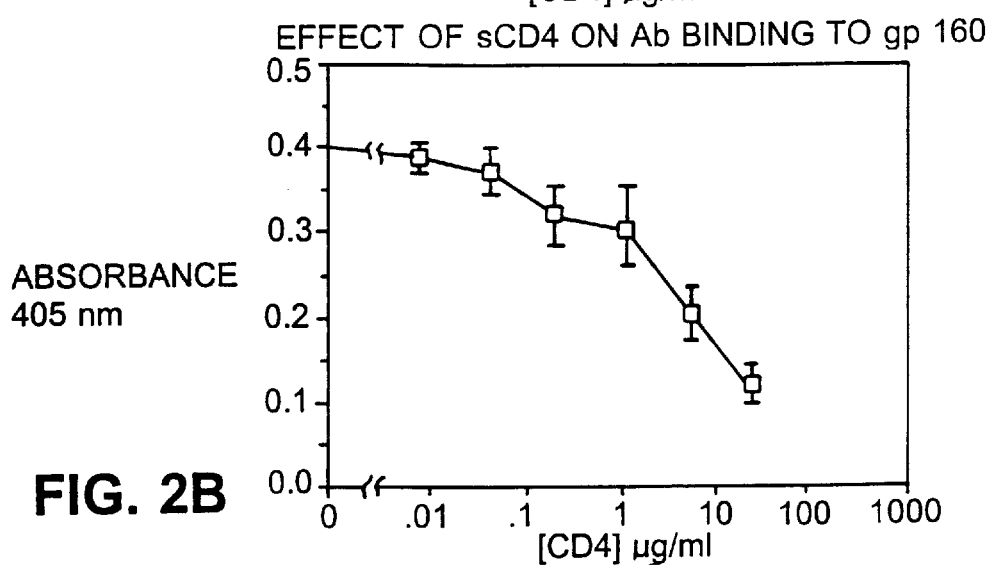
Figure 2C:
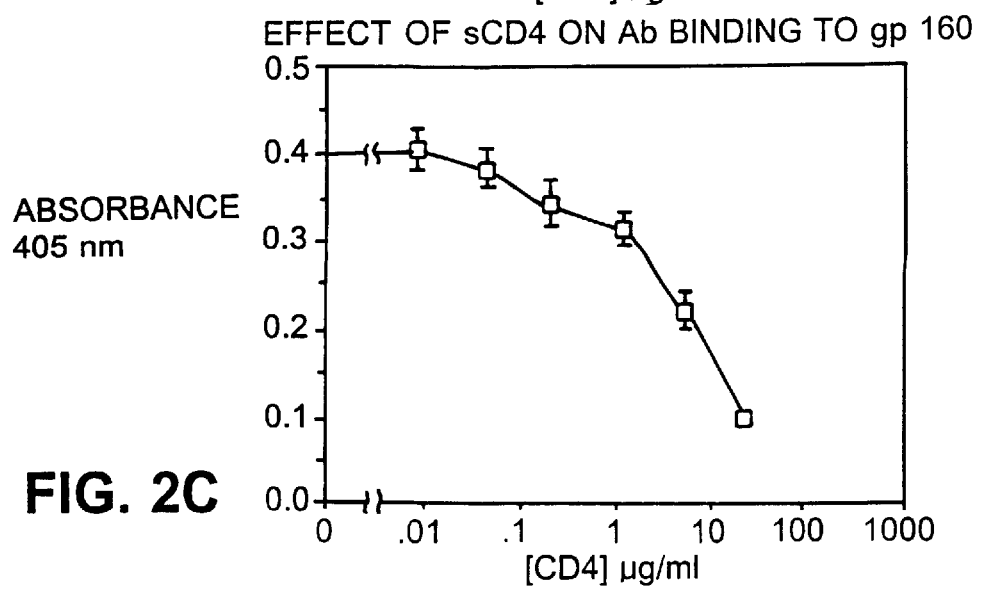

The results are shown in FIG. 2. In FIG. 2A the open squares represent supernatant from 50–69, an anti-gp41 human mAb [Gorny, M. K., V. Gianakakos, S. Sharpe, and S. Zolla-Pazner (1989) Proc. Natl. Acad. Sci. USA 86:1624–1628]. The closed diamonds in FIG. 2A represent supernatant from 1125H. FIG. 2B shows results for supernatant from 2173C. FIG. 2C shows results for supernatant from 2154B.1. The results show that the binding of the 50–69 (control mAb) to gp160 is not inhibited by soluble CD4, whereas that of the other three mabs (1125H, 2173C, 2154B.1) is inhibited by soluble CD4 in a concentration-dependent fashion. The differences in absorbance observed for the four human mAbs in the absence of soluble CD4 are due to differences in the absolute concentrations and/or affinities of the mAbs in the supernatants tested. Taking the concentration of mAb in each of the experiments into account, CD4 inhibited each of the mAbs' binding to gp160 to approximately the same extent.

These results indicate that: a) the epitope(s) recognized by these mAbs is in or near the CD4 binding site or b) CD4 binding to gp160 creates a conformational change in the latter which causes the epitope(s) of the mAbs to become inaccessible. We believe, based on studies of the binding of this antibody to site specific mutants of gp120 that the epitope is in fact part of the CD4 binding site.

Affinities of mAbs

The affinity of mAbs for gp160 or $V3_{MN}$ was determined by diluting mAbs of known concentration and assaying the various dilutions on gp160 or $V3_{MN}$ coated plates by ELISA as discussed above. It has been demonstrated that the concentration at which half-maximal Ab binding is observed is a rough value of 1/K [van Heyningen, V., and S. van Heyningen. (1987) in Methods of Hybridoma Formation, A. H. Bartal, and Y. Hirshaut (ed.). Humana Press, Clifton, N.J., p. 399–411].

Results of these measurements are shown in Table 1. Antibodies with K values in the vicinity of $10^9$ L/mole are considered to be of high affinity [Berzofsky, J. A., S. L. Epstein, and I. J. Berkower.(1989) in Fundamental Immunology, Second Edition, W. E. Paul (ed.). Raven Press, Ltd., New York, p. 315–356]; by this criterion, all four of our mAbs possess high affinity for gp120.

Chain Isotypes

The heavy chain isotype of each of the 1125H, 2173C, 2154B.1 and 4117C mAbs was determined to be IgG1. The light chain isotype of each of the three anti-CD4 binding site mabs was determined to be kappa whereas that of 4117C was found to be lambda. These results were obtained as described above.

Neutralization Abilities

The results of the in vitro neutralization assays indicate that human mabs 1125H, 2173C and 2154B.1 have potent neutralizing abilities against HIV-1 strains: IIIB, MN, SF-2 and RF.

The potent neutralizing activity of 1125H against the MN strain is shown in FIG. 3.

Human mAb 4117C had potent neutralization against the MN and SF-2 strains, as shown in FIGS. 6 and 7 respectively. In the fluorescence focus assay approximately $1\times10^5$ infectious units of virus were incubated with the concentrations of single HuMAbs or an equimolar mixture of the two HuMAbs as shown in the figure, and infection was measured after 24 hours. The inset shows the same results plotted on a different abscissa scale.

Destruction of the gp120 epitope of mAbs 1125H, 2173C and 2154B.1 upon reduction Western blot analysis of 1125H mAb on reduced or non-reduced HIV-1 lysate was performed as described above.

On the non-reduced lysate strip, bands at 120 kD were observed (data not shown), while on the reduced strip, no reaction of the mabs with the HIV-1 lysate was seen. These results indicate that the epitope(s) of the mAbs is destroyed by reduction of disulfide bonds.

Quantitation of human mAbs

These determinations were made by ELISA using goat anti-human IgG (Zymed) (10 μg/ml in 1% BSA in PBS) to coat the plates and to capture the human Ab in supernatants or purified Ab preparations [Gorny, M. K., V. Gianakakos, S. Sharpe, and S. Zolla-Pazner. (1989) Proc. Natl. Acad. Sci. USA 86:1624–1628]. The bound human Ab was detected with goat anti-human IgG conjugated to alkaline phosphatase (Zymed), and a standard curve was produced for each assay using affinity-purified human IgG (Cappel) of known concentration.

Competition Assay for Screening Culture Supernatants or Human Serum

A competition assay can be performed in order to screen culture supernatants or human serum for antibody against the epitopes, or epitope clusters, which the mAbs of the invention are specific for. The competition assay is carried out essentially as described above for the competition assay with CD4. However, biotin-labeled mAbs from cell line 1125H, 2173C, 2154B.1 or 4117C are used in competition with supernatant from the culture screened to bind to gp160 or V3$_{MN}$ coated ELISA wells. Binding of the biotin labeled mAb is detected by a subsequent incubation with alkaline phosphatase-conjugated streptavidin. Normal human serum or supernatant containing human IgG not specific for the epitope are used as negative controls.

Specificity of anti-V3 antibody 4117C 4117C was found to recognize a variety of divergent HIV strains, including MN, SF-2, FV (New York), 11699 (Central Africa), and the JR-CSF primary isolate (Los Angeles) (Koyanagi et al. 1987). 4117C human mAb is less strain specific than other anti-V3 human mAbs that have been described (Scott et al. 1990, Zolla-Pazner et al. 1990). Comparison of the V3 sequences of the isolates recognized by 4117C reveals that the sequence Gly Pro Gly Arg (SEQ ID NO:3) at the tip of the loop is shared by all of them. In addition, the sequence Ile Xaa Ile (SEQ ID NO:4) just to the left of the Gly Pro Gly Arg (SEQ ID NO:3) is highly conserved among these isolates. These observations indicate that 4117C may be directed against a relatively conserved sequence near the tip of the loop. The Gly Pro Gly Arg Ala Phe sequence (SEQ ID NO:1) sequence at the tip of the loop has recently been shown to induce broadly reactive anti-V3 Abs in experimental animals (Javaherian et al. 1990). FIGS. 6 and 7 show that human mAb 4117C exhibits potent neutralizing activity against the MN and SF-2 strains of HIV, respectively.

Synergistic neutralization of HIV by human mAbs 1125H and 4117C.

An exciting new discovery is that certain antibodies against the CD4 binding site and certain antibodies against the V-3 loop synergize to neutralize HIV.

1125H human mAb against the CD4 binding site synergizes with our 4117C human mAb against the V3 loop to neutralize HIV. FIG. 6 shows that an equimolar mixture of the two human mAbs neutralizes the MN strain of HIV significantly better than either of the two human mAbs alone. The mixture of human mAbs effects 50% neutralization of virus at approximately a 5 fold lower concentration than that of either human mAb alone, meaning that each of the individual human mAbs is 10 fold more effective when mixed with the other human mAb than when used alone. This is a dose reduction index of 10 for each of the human mAbs at the 50% neutralization level. When higher, more physiologically significant, levels of neutralization are examined, the synergistic effect is even more dramatic. Mathematical analysis of the results shown in FIG. 6 indicates that at 95% neutralization, dose reduction indices of 57 and 29 are obtained for 1125H and 4117C, respectively, whereas at 99% neutralization, dose reduction indices of 156 and 54 are obtained for these human mAbs. We have also demonstrated synergistic neutralization of the SF-2 strain of HIV by human mAbs 1125H and 4117C (FIG. 7). The results are impressive though not as profound as those seen with the MN strain. This is probably due to the fact that neither of the human mAbs individually has as great a neutralizing activity for the SF-2 strain as for the MN strain. The dose reduction indices for 50% neutralization of SF-2 are 9 and 4 for 1125H and 4117C, respectively, whereas those at 95% neutralization are 57 and 9 for these human mAbs.

Figure 8A:
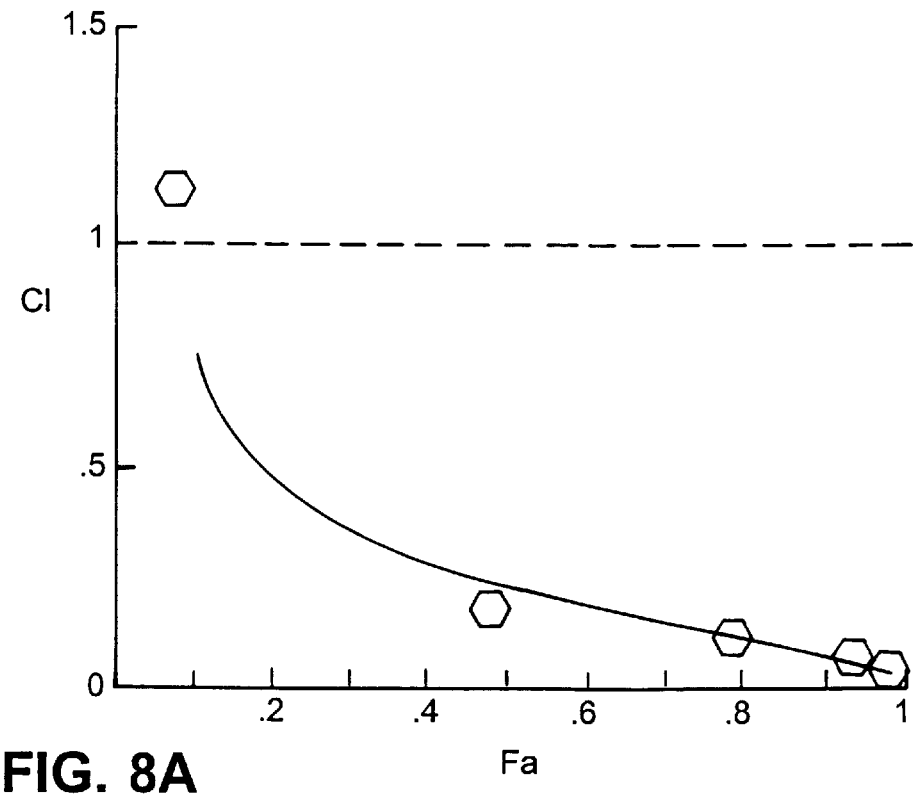
FIGS. 8a and 8b depict combination index values calculated from experimental curves shown in FIGS. 6 and 7.
Figure 8B:
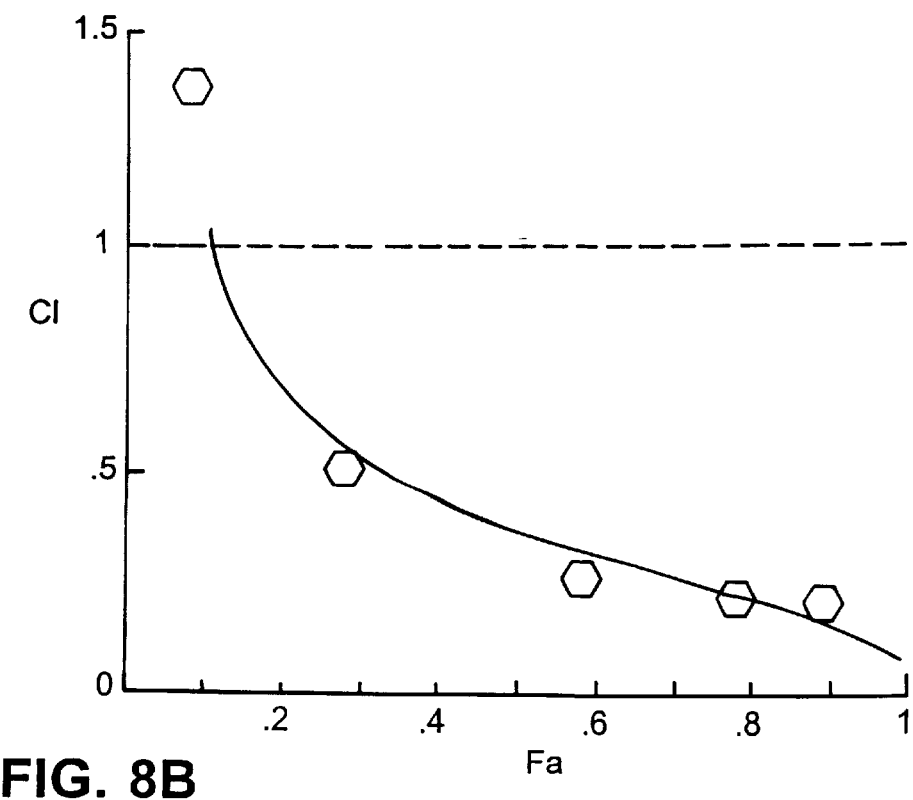

We have analyzed the degree of synergism between 1125H and 4117C. The results indicate that the synergism which we have observed against the MN strain is as great as any yet seen between any two drugs or antibodies, i.e., +4 synergism, whereas that against the SF-2 strain is a +3 synergism, on a scale of +1 to +4 (Chou 1991). These values are assigned based on the combination index (CI) values calculated from experimental curves such as those shown in FIGS. 6 and 7. CI values less than 1 indicate synergy (Chou and Talalay 1984). FIG. 8 shows the CI plots calculated from our experimental results (FIGS. 6 and 7). CI is plotted versus $F_a$, where $F_a \times 100$=the % neutralization observed, i.e. Fa=% neutralization/100. Calculation of combination index values is well known in the art.

Figure 9:
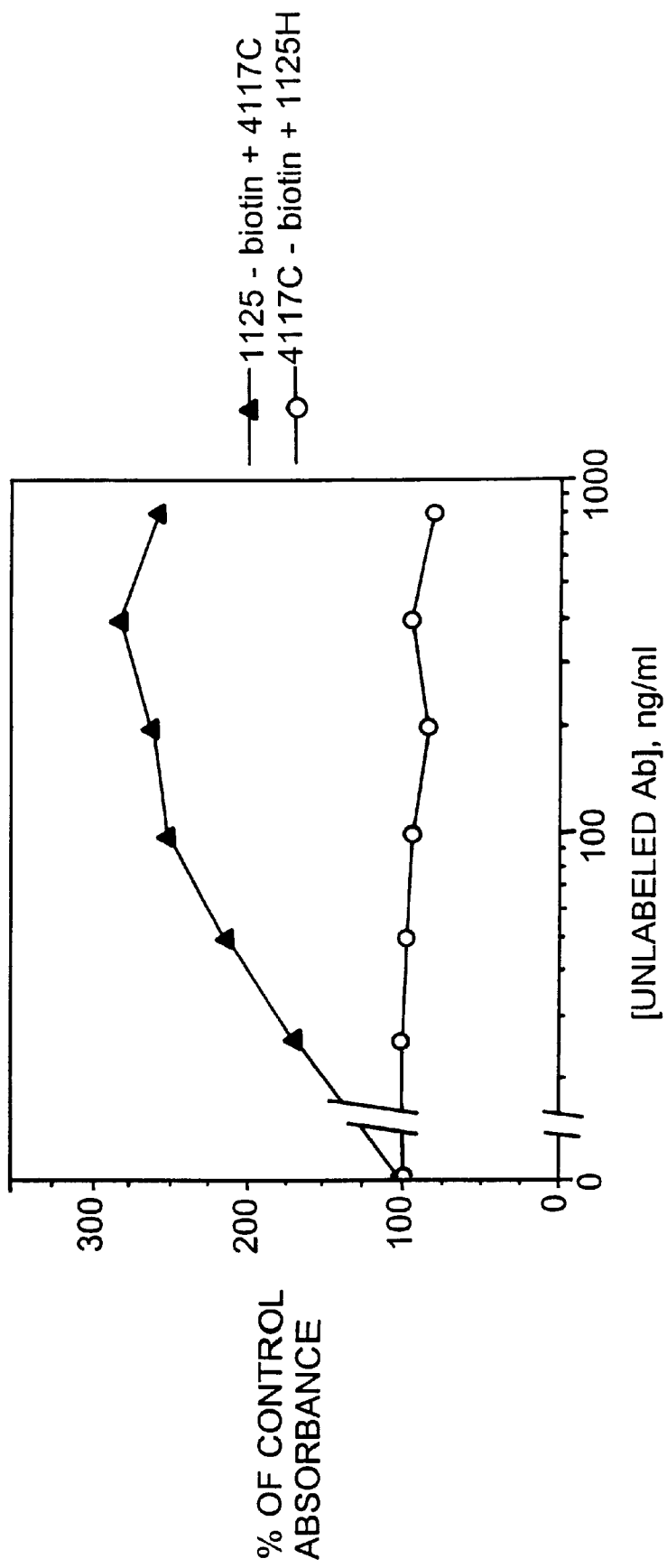
FIG. 9 depicts results of an experiment measuring the effect of 1125H on binding of 4117C to gp160 MN and visa versa.

In order to address the mechanism of this synergistic neutralization, the effect of 4117C on the binding of 1125H to its gp120 epitope and vice versa has been evaluated. To carry out these experiments, one of the human mabs was tagged with biotin, and mixed with different amounts of the second, unlabeled an tibody. Bound biotinylated antibodies were then detected by the binding of streptavidin in an ELISA assay. The antigen used was recombinant gp160 of the MN strain that contains the relevant gp120 epitopes bound by both of the human mAbs. We have consistently been able to observe a 2–3 fold increase in 1125H-biotin binding to gp160$_{MN}$ in the presence an equimolar concentration of 4117C, whereas 4117C-biotin binding to gp160$_{MN}$ appears to be unaffected b y 1125H (FIG. 9). Our working hypothesis based on these results has been presented in FIG. 5.

Derivation and characteristics of a new HuMab against the CD4 binding site, 5145A Cell line 5145A was derived by the same protocol as 1125H. Cell line 5145A was deposited with the American Type Culture Collection, 12301 Parklawn Drive, Rockville, Md. 10852, on Mar. 10, 1992, and has been assigned accession number CRL 10982. The 5145A HuepAb has the following characteristics. Its binding to gp160 is inhibited by soluble CD4 similarly to that of 1125H, and its epitope is destroyed by reduction, also similar to that of 1125H. Its apparent affinity constant is $1 \times 10^9$ L/mole. It is an IgG HuMAb; its IgG subclass remains to be determined. Its light chain is of the kappa isotype. Like 1125H, 5145A reacts with MN-, IIB- and RF-infected cells by immunofluorescence. However, 5145A recognizes a different epitope of the CD4 binding site than 1125H based on its neutralization of the 4 HIV-1 strains mentioned above. Specifically, 1125H neutralizes the IIIB, SF-2, and MN strains significantly better than the RF and SF-2 strains, whereas the 5145A HuMAb exhibits virtually identical neutralization of the 4 strains discussed and at levels comparable to the 1125H HuMAbs neutralization of the MN strain (see FIG. 6). This difference in pattern of strain neutralization must be due to a difference in epitope specificity of the 5145A and 1125H HuMAbs, since they posses comparable affinity for gp120.

Synergistic neutralization of the MN and SF-2 strains of HIV-1 by 5145A and 4117C.

Figure 10:
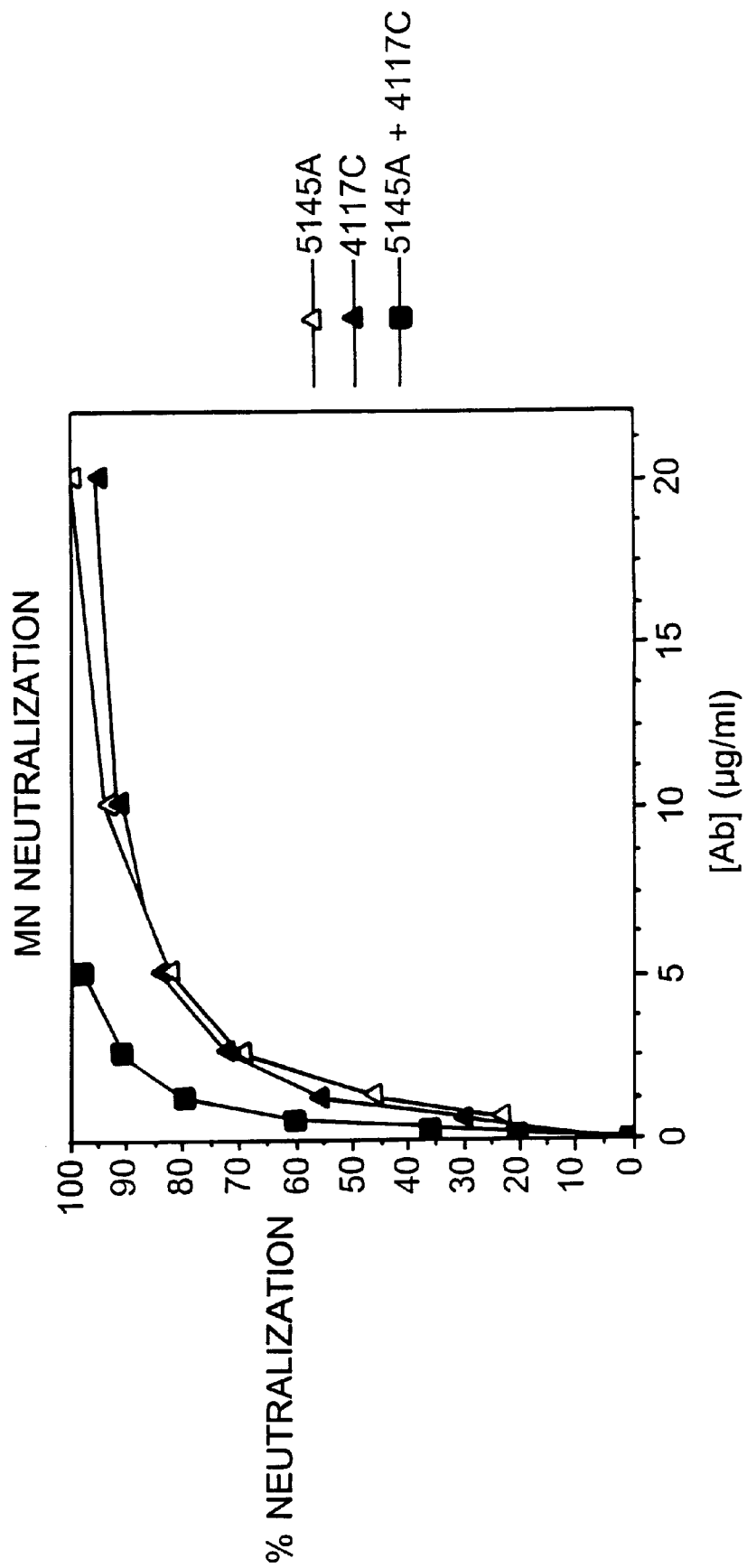
FIG. 10 depicts the synergistic neutralization of the MN strain by human mAbs 5145A and 4117C.
Figure 11:
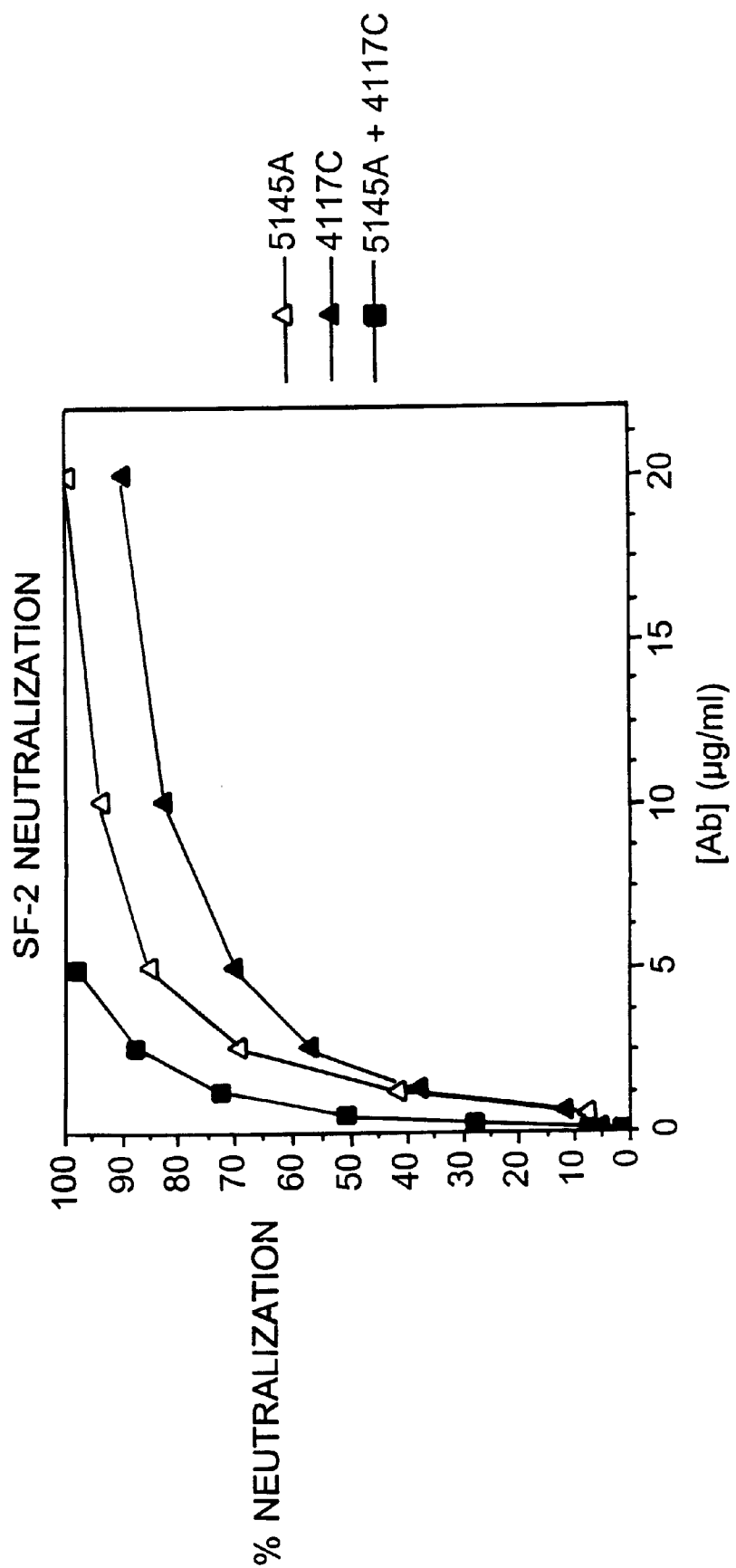
FIG. 11 depicts the synergistic neutralization of the SF-2 strain by human mAbs 5145A and 4117C.

Used at a 1:1 molar ratio, HuMAbs 5145A (anti-CD binding site) and 4117C (anti-V3) synergistically neutralize MN and SF-2 strains, as seen in FIGS. 10 and 11, respectively. This demonstrates that anti-CD4 binding site HuMAbs of differing epitope specificities (1125H and 5145A) can participate in synergistic neutralization with an antibody against the V3 loop.

Isolation and characterization of chimpanzee anti-V3 Abs from serum of an animal hyperimmunized with V3 peptide Chimpanzee #499 was immunized with V3 peptide as described in Girard et al. 1991 (PNAS paper) and serum taken at the peak of neutralizing Ab titer (also shown in op.

cit.). The anti-V3 Abs were purified on an affinity column with V3 peptide of IIIB strain attached as described below. The chimpanzee Ab concentration was determined as described for the HuMAbs, except that the IgM, IgA, and IgG concentrations were determined in separate assays with purified human Ab standards of each isotype. The total chimpanzee anti-V3 Ab concentration was taken to be the sum of the concentrations of these three antibody classes. In a previous paper (Tilley et al. 1991, Res. Virol. in press) we have shown that this chimpanzee anti-V3 Ab's binding to the V3 loop is destroyed by spontaneous proteolytic cleavage of V3, indicating that its epitope is on the right (C-terminal) side of the loop near the tip. In contrast, we believe that our anti-V3 HuMAb, 4117C is directed toward an epitope overlapping the tip of the loop. The assignment of these epitopes correlates with the observation that the chimpanzee anti-V3 Abs are strain-specific (Girard et al. 1991, PNAS), whereas our anti-V3 HuMAb 4117C recognizes a variety of divergent HIV-1 strains, i.e., is against a conserved epitope involving the tip of the loop.

Figure 12:
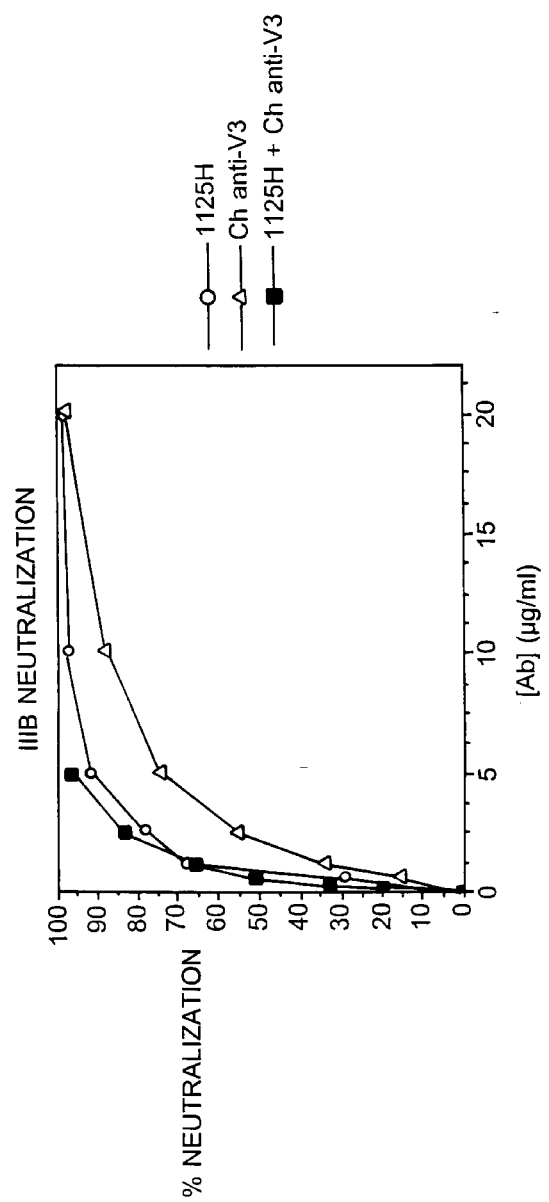
FIG. 12 depicts the synergistic neutralization of the IIIb strain by chimp anti-V3 Abs and 1125H.

Synergistic neutralization of the IIIB strain of HIV-1 by anti-V3 chimp Abs and 1125H (anti-CD4 binding site HuMAb) FIG. 12 shows that chimp anti-V3 Abs and 1125H mixed at 1:1 molar ratio synergistically neutralize the IIIb strain. This is significant not only because it shows that anti-V3 Abs against different epitopes can participate in synergistic neutralization (chimp anti-V3 and 4117C), but also because it includes another HIV-1 strain, i.e., IIIB, in our observations of synergistic neutralization.

Supplemental List of References

Anderson, L. J., Bingham, P., and Hierholzer, J. D. (1988). Neutralization of respiratory syncytial virus by individual and mixtures of F and G protein monoclonal antibodies. J. Virol. 62, 4232–4238.

Berman, P. W., Riddle, L., Nakamura, G., Haffar, O. K., Nunes, W. M., Skehel, P., Byrn, R., Groopman, J., Matthrews, T., and Gregory, T. (1989). Expression and immunogenicity of the extracellular domain of the human immunodeficiency virus type 1 envelope glycoprotein, gp160. J. Virol. 63, 3489–3498.

Berman, P. W., Gregory, T. J., Riddle, L., Nakamura, G. R., Champe, M. A., Porter, J. P., Wurm, F. M., Hershberg, R. D., Cobb, E. K., and Eichberg, J. W. (1990). Protection of chimpanzees from infection by HIV-1 after vaccination with recombinant glycoprotein gp120 but not gp160. Nature. 345, 622–625.

Chou, T., and Talalay, P. (1984). Quantitative analysis of dose-effect relationships: The combined effects of multiple drugs or enzyme inhibitors. Adv. in Enz. Regulation. 22, 27–55.

Chou, T., (1991). The median-effect principle and the combination index for quantitation of synergism and antagonism. in: Synergism and antagonism in chemotherapy, T. Chou, and D. C. Rideout, eds. (San Diego, Calif.: Academic Press), pp. 61–102. Cleff, J. C. S., Chanas, A. C., and Gould, E. A. (1983). Conformational changes in Sindbis glycoprotein E1 induced by monoclonal antibody binding. J. Gen. Virol. 64, 11221–1126.

Coller, H. A., and Coller, B. S. (1987). Statistical assessment of hybridoma monoclonality after subcloning by the limiting dilution technique. in: Methods of Hybridoma Formation, A. H. Bartal, and Y. Hirshaut, eds. (Clifton, N.J.: Humana Press), pp. 231–236.

Crawford, D. H. (1985). Production of human monoclonal antibodies using Epstein-Barr virus. in: Human Hybridomas and Monoclonal Antibodies, E. g. Engleman, S. K. H. Foung, J. Larrick, and A. Raubitschek, eds. (New York: Plenum Press), pp. 37–53.

Devash, Y., Calvelli, T. A., Wood, D. G., Reagan, K. L., and Rubinstein, A. (1990). Vertical transmission of human immunodeficiency virus is correlated with the absence of high-affinity/avidity maternal antibodies to the gp120 principal neutralizing domain. Proc. Natl. Acad. Sci. USA. 87, 3445–3449.

Dubuisson, J., Guillaume, J., Boulanger, D., Thiry, E., Bublot, M., and Pastoret, P. (1990). Neutralization of bovine herpervirus type 4 by pairs of monoclonal antibodies raised against two glycoproteins and identification of antigenic determinants involved in neutraliziation. J. Gen. Virol. 71, 647–653.

Emini, E. A., Nara, P. L., Schleif, W. A., Lewis, J. A., Davide, J. P., Lee, D. R. Kessler, J., Conley, S., Matsushita, S., Putney, S. D., Gerety, R. J., and Eichberg, J. W. (1990). Antibody-mediated in vitro neutralization of human immunodeficiency virus type 1 abolishes infectivity for chimpanzees. J. Virology. 64, 3674–3678.

Gerna, G., Revello, M. G., Dovis, M., Petruzzelli, E., Achilli, G., Percivalle, E., and Torsellini, M. (1987). Synergistic neutralization of rubella virus by monoclonal antibodies to viral haemagglutinin. J. Gen. Virol. 68, 2007–2012.

Girard, M., Kieny, M.P., Pinter, A., Barre-Sinoussi, F., Nara, P., Kolbe, H., Kusumi, K., Chaput, A., Reinhart, T., Muchmore, E., Ronco, J., Kaczorek, M., Gomard, E., Gluckman, J., and Fultz, P. (1991). Immunization of chimpanzees confers protection against challenge with human immunodeficiency virus. Proc. Natl. Acad. Sci, USA. 88, 542–546.

Ho, D. D., Sarngadharan, M. G. Hirsch, M. S., Schooley, R. T., Rota, T. R., Kennedy, R. C., Chanh, T. C., and Sato, V. L. (1987). Human immunodeficiency virus neutralizing antibodies recognize several conserved domains on the envelope glycoproteins. J. Virol. 61, 2024–2038.

Ho., D. D., McKeating, J. A., Li, X. L., Moudgil, T., Daar, E. S., Sun, N., and Robinson, J. E. (1991). Conformational epitope on gp120 important in CD4 binding and human immunodeficiency virus type 1 neutralization identified by a human monoclonal antibody. J. Virol. 65, 489–493.

Homsy, J., Tateno, M., and Levy, J. A. (1988). Antibody-dependent enhancement of HIV infection. Lancet. i, 1285–1286.

Javaherian, K., Langlois, A. J., LaRosa, G. J., Profy, A. T., Bolognesi, D. P., Herlihy, W. C., Putney, S. D., and Matthews, T. J. (1990). Broadly neutralizing antibodies elicited by the hypervariable neutralizing determinant of HIV-1. Science. 250, 1590–1593.

Jouault, T., Chapuis, F., Olivier, R., Parravicini, C., Bahraoui, E., and Gluckman, J. C. (1989). HIV infection of monocytic cells: role of antibody-mediated virus binding to Fc-gamma receptors. AIDS. 3, 125–133.

Karpas, A., Hill, F., Youle, M., Cullen, V., Gray, J., Byron, N. Hayhoe, F., Tenant-Flowers, M., Howard, L., Gilgen, D., J. K. Oates, Hawkins, D., and Gazzard, B. (1988). Effects of passive immunization of patients with the acquired immunodeficiency syndrome-related complex and acquired immunodeficiency syndrome. Proc. Natl. Acad. Sci. USA. 85, 9234–9237.

Kieny, M. P., Lathe, R., Riviere, Y., Dott, K., Schmitt, D., Girard, M., Montagnier, L., and Lecocq, J. (1988). Improved antigenicity of the IIIV env protein by cleavage site removal. Protein Engineering. 2, 219–225.

Kimura-Kuroda, J., and Yasui, K. (1983). Topographical analysis of antigenic determinants on envelope glycoprotein V3 (E) of Japanese encephalitis virus, using monoclonal antibodies. J. Virol. 45, 124–132.

Kingsford, L. (1984). Enhanced neutralization of La Crosse virus by the binding of specific pairs of monoclonal antibodies to the G1 glycoprotein. Virology. 136, 265–273.

Koyanagi, Y., Miles, S., Mitsuyasu, R. T., Merrill, J. E., Vinters, H. V., and Chen, I. S. Y. (1987). Dual infection of the central nervous system by AIDS viruses and distinct cellular tropisms. Science 236, 819–822.

LaRosa, G. J., Davide, J. P., Weinhold, K., Waterbury, J. A., Profy, A. T., Lewis, J. A., Langlois, A. J., Dreesman, G. R., Boswell, R. N., P. Shadduck, Holley, L. H., Karplus, M., Bolognesi, D. P., Matthews, T. J., Emini, E. A., and Putney, S. D. (1990). Conserved sequence and structural elements in the HIV-1 principal neutralizing determinant. Science. 249, 932–935.

Lasky, L. A., Nakamura, G., Smith, D. H., Fennie, C., Shimasaki, C., Patzer, E., Berman, P. Gregory, T., and Capon, D. J. (1987). Delineation of a region of the human immunodeficiency virus type 1 gp120 glycoprotein critical for interaction with the CD4 receptor. Cell. 50, 975–985.

Layne, S. P., Spouge, J. L., and Dembo, M. (1989). Quantifying the infectivity of human immunodeficiency virus. Proc. Natl. Acad. Sci. USA 86, 4644–4648.

Ljunggren, K., Bottiger, B., Biberfeld, G., Karlson, A., Fenyo, E., and Jondal, M. (1987). Antibody-dependent cellular cytotoxicity-inducing antibodies against human immunodeficiency virus. J. Immunol. 139, 2263–2267.

Lussenhop, N. O., Goertz, R., Wabuke-Bunoti, M., Gehrz, R., and Kara, B. (1988). Epitope analysis of human cytomegalovirus glycoprotein complexes using murine monoclonal antibodies. Virology. 164, 362–372.

Olshevsky, U., Helseth, E., Gurman, C., Li, J., Haseltine, W., and Sodroski, J. (1990). Identification of individual human immunodeficiency virus type 1 gp120 amino acids important for CD4 receptor binding. J. Virol. 64, 5701–5707.

Peiris, J. S. M., Porterfield, J. S., and Roehrig, J. T., (1982). Monoclonal antibodies against the flavivirus West Nile. J. Gen. Virol. 58, 283–289.

Posner, M., Mukherjee, M., Hideshima, T., Cannon, T. C., and Mayer, K. (1990). Development of an IgG-1 human monoclonal antibody that neutralizes HIV1 infectivity and binding and reacts with a cell surface antigen expressed by HIV1 infected cells. Sixth International Conference on AIDS, San Francisco. Abstract, Th.A.77.

Robert-Guroff, M., Brown, M., and Gallo, R. C. (1985). HTLV-III-neutralizing antibodies in patients with AIDS and AIDS-related complex. Nature. 316, 72–74.

Robinson, W. E., Kawamura, T., Lake, D., Masuho, Y., Mitchell, W. M., and Hershy, E. M. (1990). Antibodies to the primary immunodominant domain of human immunodeficiency virus type 1 (HIV-1) glycoprotein gp41 enhance HIV-1 infection in vitro. J. Virol. 64, 5301–5305.

Robinson, J. E., Holton, D., Pacheco-Morell, S., Liu, J., and McMurdo, H. (1990). Identification of conserved and variant epitopes of human immunodeficiency virus type 1 (HIV-1) gp120 by human monoclonal antibodies produced by EBV-transformed cell lines. AIDS Res. Human Retroviruses. 6, 567–579.

Rook, A. H., Lane, H. C., Folks, T., McCoy, S., Alter, H., and Fauci, A. S. (1987). Sera from HTLV-III/LAV antibody-positive individuals mediate antibody-dependent cellular cytotoxicity against HTLV-III/LAV-infected T cells. J. Immunol. 138, 1064–1067.

Russell, P. H. (1986). The synergistic neutralization of Newcastle Disease virus by two monoclonal antibodies to its haemagglutinin-neuraminidase protein. Arch. Virol. 90, 135–144.

Scott, C. F., Silver, S., Profy, A. T., Putney, S. D., Langlois, A., Weinhold, K., and Robinson, J. E. (1990). Human monoclonal antibody that recognizes the V3 region of human immunodeficiency virus gp120 and neutralizes the human T-lymphotropic virus type III MN strain. Proc. Natl. Acad. Sci. USA. 87, 8597–8601.

Sun, N., Ho, D. D., Sun, C. R. Y., Liou, R., Gordon, W., Fung, M. S. C., Li, X., Ting, R. C., Lee, T., Chang, N. T., and Chang T. (1989). Generation and characterization of monoclonal antibodies to the putative CD4-binding domain of human immunodeficiency virus type 1 gp120. J. Virol. 63, 3579–3585.

Takeda, A., Tuazon, C. U., and Ennis, F. A. (1988). Antibody-enhanced infection by HIV-1 via Fc receptor-mediated entry. Science. 242, 580–583.

Tilley, S. A., Honnen, W. J., Racho, M., Hilgartner, M., and Pinter, A. (1991). A human monoclonal antibody against the CD4 binding site of HIV-1 gp120 exhibits potent, broadly neutralizing activity. Res. Virol. Accepted for publication.

Volk, W. A., Snyder, R. M., Benjamin, D. C., and Wagner, R. R. (1982). Monoclonal antibodies to the glycoprotein of vesicular stomatitis virus: Comparative neutralizing activity. J. Virol. 42, 220–227.

Weiss, R. A., Clapham, P. R., Cheingsong-Popov, R., Dalgleish, A. G., Carne, C. A., Weller, I. V. D., and Tedder, R. S. (1985). Neutralization of human T-lymphotropic virus type III by sera of AIDS and AIDS-risk patients. Nature. 316, 69–71.

Zolla-Pazner, S., Gianakakos, V., Williams, C., Sharpe, S., and Gorny, M. K. (1990). Production of human monoclonal antibodies against the V3 loop of gp120. Sixth International Conference on AIDS, San Francisco. Abstract, Th.A. 75.

What is claimed is:

1. A composition of antibodies comprising an effective amount of:

(a) purified antibodies specific for the V3 loop of HIV-1 envelope glycoprotein gp120; and (b) purified antibodies specific for the CD-4 binding site of HIV-1 envelope glycoprotein gp120;
   wherein the composition synergistically neutralizes HIV-1 infectivity.

2. The composition of claim 1 having a combination index value less than 1 at 50% neutralization of $10^4$ to $10^5$ infectious units of HIV-1 at a concentration no greater than 100 micrograms per milliliter of said antibodies.

3. The composition of claim 2 which neutralizes 50% of $1 \times 10^4$ infectious units of the SF-2 strain of HIV-1 in a 24 hour assay at a concentration of 1.2 micrograms per milliliter of said antibodies.

4. The composition of claim 1 having a combination index value less than 0.5 at 50% neutralization of $10^4$ to $10^5$ infectious units of HIV-1 at a concentration no greater than 100 micrograms per milliliter of said antibodies.

5. The composition of claim 1 which neutralizes 50% of $1 \times 10^4$ infectious units of the MN strain of HIV-1 in a 24 hour assay at a concentration of 0.15 micrograms per milliliter of said antibodies.

6. The composition of claim 1 which neutralizes at least 95% of $1 \times 10^4$ infectious units of the SF-2 strain of HIV-1 in a 24 hour assay at a concentration of 7 micrograms per milliliter of said antibodies.

7. A composition of human monoclonal antibodies comprising an effective amount of:
   (a) human monoclonal antibodies specific for the V3 loop of HIV-1 envelope glycoprotein gp120; and
   (b) human mnonoclonal antibodies specific for the CD-4 binding site of HIV-1 envelope glycoprotein gp120;
   wherein the composition synergistically neutralizes HIV-1 infectivity.

8. The composition of claim 7 having a combination index value less than 1 at 50% neutralization of $10^4$ to $10^5$ infectious units of HIV-1 at a concentration no greater than 100 micrograms per milliliter of said antibodies.

9. The composition of claim 8, wherein the combination index value is less than 0.5.

10. The composition of human monoclonal antibodies of claim 7 which achieves at least 95% neutralization of $1 \times 10^4$ infectious units of the MN strain of HIV-1 in a 24 hour assay at a concentration of 0.5 micrograms per milliliter of said antibodies.

11. The composition of human monoclonal antibodies of claim 7 wherein the human monoclonal antibodies which are specific for the CD4 binding site
   (a) neutralize HIV-1 strains IIIB, MN, SF-2 and RF;
   (b) does not specifically bind with LAV-2;
   (c) specifically bind with both acetone and methanol-fixed HIV-1 infected cells;
   (d) specifically bind with formaldehyde-fixed HIV-1 infected cells;
   (e) specifically bind with live HIV-1 infected cells;
   (f) possess high affinity for gp120;
   (g) do not specifically bind with the hypervariable V3 loop of gp120;
   (h) are inhibited from binding to gp120 in the presence of CD4;
   (i) achieves 50% neutralization of the MN HIV-1 strain in a 24 hour assay at a concentration of 1 microgram per milliliter of said antibodies in the absence of other antibodies; and
   (j) does not specifically bind with HIV-1 which has been treated to reduce disulfide bonds of the virus' protein.

12. The composition of human monoclonal antibodies of claim 7 which achieves 50% neutralization of $1 \times 10^4$ infectious units of the MN strain of HIV-1 in a 24 hour assay at a concentration of 0.15 micrograms per milliliter of said antibodies.

13. The composition of human monoclonal antibodies of claim 7 which also synergistically neutralizes the SF-2 strain.

14. The composition of human monoclonal antibodies of claim 7 which achieves 50% neutralization of $1 \times 10^4$ infectious units of the SF-2 strain of HIV-1 in a 24 hour assay at a concentration of 1.2 micrograms per milliliter of said antibodies.

15. A composition of antibodies consisting essentially of an effective amount of:
   (a) human monoclonal antibodies which competitively inhibit the binding of antibodies produced by the cell line 1125H having A.T.C.C. accession no. CRL 10582 to gp120; and
   (b) human monoclonal antibodies which competitively inhibit the binding of antibodies produced by the cell line 4117C having A.T.C.C. accession no. CRL 10770 to gp120,
   wherein the composition synergistically neutralizes HIV-1 infectivity.

16. The composition of human monoclonal antibodies of claim 15 which neutralizes 95% of $1 \times 10^4$ infectious units of the MN strain of HIV-1 in a 24 hour assay at a concentration of 0.5 micrograms per milliliter of said antibodies.

17. A composition of human monoclonal antibodies comprising an effective amount of:
   (a) human monoclonal antibodies hating the epitope specificity of antibodies produced by the cell line 1125H having A.T.C.C. accession no. CRL 10582, and
   (b) human monoclonal antibodies having the epitope specificity of antibodies produced by the cell line 4117C having A.T.C.C accession no CRL 10770,
   wherein the composition synergistically neutralizes HIV-1 infectivity.

18. The composition of human monoclonal antibodies of claim 17 which achieves at least 95% neutralization of $1 \times 10^4$ infectious units of the MN strain of HIV-1 in a 24 hour assay at a concentration of 0.5 micrograms per milliliter of said antibodies.

19. The composition of human monoclonal antibodies of claim 17 comprising
   (a) human monoclonal antibodies having all the identifying characteristics of those obtained from the cell line 1125H having A.T.C.C. accession no. CRL 10582; and
   (b) human monoclonal antibodies having all the identifying characteristics of those obtained from the cell line 4117C having A.T.C.C. accession no. CRL 10770.

20. The composition of claim 17 comprising human monoclonal antibodies obtained from cell line 1125H having A.T.C.C. accession no. CRL 10582 and human monoclonal antibodies obtained from cell line 4117C having A.T.C.C. accession no. CRL 10770.

21. The composition of claim 17 wherein the antibodies are in a molar ratio of 1:1.

22. A cell line which produces human monoclonal antibodies specific for the V3 loop of HIV-envelope glycoprotein gp120, which antibodies are specific for an envelope sequence of an HIV-1 strain that those produced by cell line 4117C having A.T.C.C. accession no. CRL 10770 are specific for, and which antibodies neutralize at least 50% of $10^4$ to $10^5$ infectious units of HIV-1 of the MN strain at an antibody concentration of about 1 microgram per milliliter of said antibodies in a 24 hour neutralization assay.

23. The cell line of claim 22 which is an EBV transformed human cell line.

24. The cell line of claim 22 which is an immortalized cell line.

25. Human monoclonal antibodies produced by the cell line of claim 22.

26. The cell line of claim 22 which produces human monoclonal antibodies that are specific for all V3 sequences that the antibody produced by cell line 4117C having accession no. CRL 10770 is specific for.

27. The human monoclonal antibodies having the epitope specificity of those produced by the cell line of claim 26.

28. Human monoclonal antibodies of claim 27 having all the identifying characteristics of those produced by the cell line 4117C having A.T.C.C. accession no. CRL 1077091.

29. The cell line of claim 28 wherein the human monoclonal antibody recognizes all of the sequences Ile Xaa Ile Gly Pro Gly Arg (SEQ ID NO:5), wherein the sequences Ile Xaa Ile Gly Pro Gly Arg (SEQ ID NO:5) are those recognized by the antibody produced by cell line 4117C, having accession no. CRL 10770.

30. Human monoclonal antibodies produced by the cell line of claim 29.

31. Human monoclonal antibodies produced by the cell line of claim 26.

32. The cell line of claim 22 wherein the human monoclonal antibody recognizes an HIV-1 strain having one of the sequences Ile Xaa Ile Gly Pro Gly Arg (SEQ ID No:5), wherein the sequences Ile Xaa Ile Gly Pro Gly Arg (SEQ ID NO:5) are recognized by the antibody produced by cell line 4117C, having accession no. CRL 10770.

33. Human monoclonal antibodies produced by the cell line of claim 32.

34. A method of treating HIV-1 comprising administering to an individual an effective amount of a composition comprising:
   (a) purified antibodies specific for the V3 loop of HIV-1 envelope glycoprotein gp120, and
   (b) purified antibodies which are specific for the CD-4 binding site of HIV-1 envelope glycoprotein gp120; wherein the composition synergistically neutralizes HIV-1 infectivity.

35. The method of claim 34 wherein said purified antibodies specific for the V3 loop of HIV-1 envelope glycoprotein gp120 are monoclonal antibodies and said purified antibodies specific for the CD4 binding site of HIV-1 envelope glycoprotein gp120 are monoclonal antibodies.

36. The method of claim 35 wherein said monoclonal antibodies are human monoclonal antibodies.

37. The method of claim 36 wherein one said monoclonal antibody is administered immediately following administration of the other monoclonal antibody.

38. The method of claim 34 wherein one said antibody is administered immediately following administration of the other antibody.

39. The method of claim 38 wherein said antibodies, in combination, achieve at least 95% neutralization in vitro of $1 \times 10^4$ infectious units of the MN strain of HIV-1 at a concentration of 0.5 micrograms per milliliter of said antibodies.

40. The method of claim 38 wherein said antibodies have a combination index value less than 1 at 50% neutralization in vitro of $10^4$ to $10^5$ infectious units of HIV-1 at a concentration no greater than approximately 100 micrograms per milliliter of said antibodies.

41. The method of claim 40, wherein the combination index value is less than 0.5.

42. The method of claim 38 wherein said antibodies are in a molar ratio of about 1:1.

43. The method of claim 38 wherein said combination achieves 50% neutralization in vitro of $1 \times 10^4$ infectious units of the MN strain of HIV-1 at a concentration of 0.15 micrograms per milliliter of said antibodies.

44. A human monoclonal antibody specific for the V3 loop of gp120 of HIV-1, said antibody having high affinity and being capable of neutralizing 50% of $10^4$ to $10^5$ infectious units of HIV-1 of the MN strain at an antibody concentration of 1 microgram per milliliter of said antibodies in a 24 hour neutralization assay.

45. The human monoclonal antibody of claim 44 capable of neutralizing 90% of $10^4$ to $10^5$ infectious units of HIV-1 of the MN strain at an antibody concentration of 5 to 10 micrograms per milliliter of said antibodies.

46. The human monoclonal antibody of claim 44 that is specific for an epitope that includes the Gly Pro Gly Arg (SEQ ID NO:3) at the tip of the V3 loop.

47. The human monoclonal antibody of claim 46 that is specific for the sequence Ile Xaa Ile Gly Pro Gly Arg (SEQ ID NO:5) at the tip of the V3 loop.

48. A cell line producing the human monoclonal antibodies of claim 44.

49. The human monoclonal antibody that is produced by cell line 4117C having A.T.C.C. accession number CRL 10770.

50. The kit for forming the composition of claim 1 which is a kit having a container of the antibodies of (a) and a container of the antibodies of (b).

51. A therapeutic reagent comprising the composition of claim 1 in a physiologically compatible solution.

52. A therapeutic reagent comprising the composition of claim 7 in a physiologically compatible solution.

53. A therapeutic reagent comprising the composition of claim 17 in a physiologically compatible solution.

* * * * *